US012599321B2

(12) United States Patent
Stahmann et al.

(10) Patent No.: US 12,599,321 B2
(45) Date of Patent: Apr. 14, 2026

(54) DEVICES AND METHODS FOR ASSESSING PULMONARY STATUS USING OPTICAL OXYGENATION SENSING

(71) Applicant: Cardiac Pacemakers, Inc., St. Paul, MN (US)

(72) Inventors: Jeffrey E. Stahmann, Ramsey, MN (US); Keith R. Maile, New Brighton, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 493 days.

(21) Appl. No.: 17/864,907

(22) Filed: Jul. 14, 2022

(65) Prior Publication Data

US 2023/0017684 A1     Jan. 19, 2023

Related U.S. Application Data

(60) Provisional application No. 63/223,201, filed on Jul. 19, 2021.

(51) Int. Cl.
*A61B 5/0205* (2006.01)
*A61B 5/00* (2006.01)
(Continued)

(52) U.S. Cl.
CPC .......... *A61B 5/1459* (2013.01); *A61B 5/0205* (2013.01); *A61B 5/14551* (2013.01);
(Continued)

(58) Field of Classification Search
CPC . A61B 5/1459; A61B 5/0205; A61B 5/14551; A61B 5/4842; A61B 5/6867;
(Continued)

(56) References Cited

U.S. PATENT DOCUMENTS 6,739,335 B1     5/2004  Rapport et al.
7,809,441 B2    10/2010  Kane et al.
(Continued)

OTHER PUBLICATIONS

Beek, J.F., et al. "The optical properties of lung as a function of respiration," Phys. Med. Biol. 42 (1997) 2263-2272 (10 pages).
(Continued)

*Primary Examiner* — Shirley X Jian
(74) *Attorney, Agent, or Firm* — Pauly, DeVries Smith & Deffner LLC

(57)     ABSTRACT

Embodiments herein relate to devices and methods for assessing pulmonary status using optical oxygenation sensing. In an embodiment, an oxygenation monitoring device can be included having a first optical emitter, wherein the first optical emitter can be configured to emit light at a first wavelength from 100 nanometers (nm) to 2000 nm. The oxygenation monitoring device and further include a first optical detector, wherein the first optical detector can be configured to detect incident light. The device can be configured so that emitted light from the first optical emitter propagates through a lung tissue and detected incident light can be used to determine an oxygenation status of the lung tissue. Other embodiments are also included herein.

17 Claims, 19 Drawing Sheets

(51) Int. Cl.
| | | |
|---|---|---|
| *A61B 5/1455* | (2006.01) | |
| *A61B 5/1459* | (2006.01) | |
| *A61B 5/024* | (2006.01) | |
| *A61B 5/08* | (2006.01) | |
| *A61B 5/091* | (2006.01) | |

(52) U.S. Cl.
CPC .......... *A61B 5/4842* (2013.01); *A61B 5/6867* (2013.01); *A61B 5/024* (2013.01); *A61B 5/0816* (2013.01); *A61B 5/091* (2013.01)

(58) Field of Classification Search
CPC ....... A61B 5/024; A61B 5/0816; A61B 5/091; A61B 5/6823; A61B 5/0803; A61B 5/14552; A61B 5/6831
See application file for complete search history.

(56) References Cited

U.S. PATENT DOCUMENTS

| | | | |
|---|---|---|---|
| 7,813,778 B2 | 10/2010 | Benaron et al. | |
| 7,865,223 B1 | 1/2011 | Bernreuter | |
| 8,126,554 B2 | 2/2012 | Kane et al. | |
| 8,320,981 B1* | 11/2012 | Mayer ................ | A61B 5/14551 |
| | | | 600/326 |
| 8,426,819 B2 | 4/2013 | Herrmann | |
| 8,794,236 B2 | 8/2014 | Phuah et al. | |
| 9,649,070 B2 | 5/2017 | Seppä et al. | |
| 10,398,863 B2 | 9/2019 | Phuah et al. | |
| 10,932,674 B2 | 3/2021 | Luxon et al. | |
| 11,154,249 B2* | 10/2021 | Kuhn ................ | A61B 5/14546 |
| 12,446,782 B2 | 10/2025 | Stahmann et al. | |
| 2002/0123674 A1 | 9/2002 | Plicchi et al. | |
| 2004/0116789 A1 | 6/2004 | Boas et al. | |
| 2006/0253016 A1 | 11/2006 | Baker et al. | |
| 2009/0163819 A1 | 6/2009 | De Kok et al. | |
| 2010/0022856 A1 | 1/2010 | Cinbis et al. | |
| 2010/0043557 A1 | 2/2010 | Savery et al. | |
| 2010/0106210 A1 | 4/2010 | Hedberg et al. | |
| 2012/0190989 A1 | 7/2012 | Kaiser et al. | |
| 2013/0310669 A1 | 11/2013 | Nitzan | |
| 2014/0149065 A1 | 5/2014 | Pompei et al. | |
| 2017/0135633 A1* | 5/2017 | Connor .............. | A61N 1/36557 |
| 2017/0303815 A1 | 10/2017 | De Limon et al. | |
| 2018/0073928 A1 | 3/2018 | Nakaya et al. | |
| 2018/0344252 A1 | 12/2018 | An et al. | |
| 2019/0320985 A1* | 10/2019 | LeBoeuf .............. | A61B 5/7271 |
| 2019/0336077 A1* | 11/2019 | Kuhn ..................... | A61B 5/486 |
| 2020/0000345 A1 | 1/2020 | Connor | |
| 2020/0029827 A1 | 1/2020 | Tang et al. | |
| 2020/0043591 A1 | 2/2020 | Kahlert et al. | |
| 2020/0268536 A1 | 8/2020 | Dilorenzo | |
| 2021/0045671 A1* | 2/2021 | Wiese .................. | A61B 5/6804 |
| 2021/0161444 A1 | 6/2021 | Shao et al. | |
| 2021/0361238 A1 | 11/2021 | Bak-Boychuk et al. | |
| 2022/0095937 A1 | 3/2022 | Faircloth | |
| 2022/0192600 A1 | 6/2022 | Bang et al. | |
| 2022/0248993 A1 | 8/2022 | Dixon | |
| 2022/0370010 A1 | 11/2022 | Zilkie et al. | |
| 2023/0014499 A1 | 1/2023 | Stahmann et al. | |
| 2023/0024917 A1 | 1/2023 | Stahmann et al. | |
| 2023/0025497 A1 | 1/2023 | Stahmann et al. | |
| 2023/0081138 A1 | 3/2023 | Stahmann et al. | |

OTHER PUBLICATIONS

Inaba, Kenti, et al. "Radiologic Evaluation of Alternative Sites for Needle Decompression of Tension Pneumothorax," Arch Surg. 2012:147(9):813-818 (6 pages).

Lichtwarck-Aschoff, Michael, et al. "Decreasing size of cardiogenic oscillations reflects decreasing compliance of the respiratory system during long-term ventilation," J. Appl. Physiol. 96; 879-884 (6 pages).

Martinsen, Paul, et al. "Temperature dependence of near-infrared spectra of whole blood," Journal of Biomedical Optics 13(3), 034016 (May/Jun. 2008) (7 pages).

Schumann, S., et al. "Cardiogenic oscillations in spontaneous breathing airway signal reflect respiratory system mechanics," Acta Anaesthesiol Scand 2011; 55: 980-986 (7 pages).

Suarez-Sipmann, Fernando, et al. "Pulmonary artery pulsatility is the main cause of cardiogenic oscillations," J Clin Monit Comput (2013) 27:47-53 (7 pages).

Tusman, Gerardo, et al. "Pulmonary blood flow generates cardiogenic oscillations," Respiratory Physiology & Neurobiology (2009) (8 pages).

Hwang, Chan-Sol, et al. "Angle-selective optical filter for highly sensitive reflection photoplethysmogram," Biomedical Optics Express 4361, vol. 8, No. 10, 2017 (8 pages).

Johnston, Hamish "New material offers angular control over light," Physics World, Mar. 27, 2014 (3 pages).

Qian, Qinyu, et al. "All-dielectric polarization-independent optical angular filter," Scientific Reports, Nov. 29, 2017, 7: 16574 (7 pages).

Zakirullin, Rustam "Creating optical filters with angular-selective light transmission," Applied Optics, 2015, vol. 54, No. 25 (5 pages).

"Non-Final Office Action," for U.S. Appl. No. 17/866,023 mailed Jul. 8, 2024 (41 pages).

"Non-Final Office Action," for U.S. Appl. No. 17/866,030 mailed May 8, 2024 (25 pages).

"Response to Non-Final Rejection," mailed on May 8, 2024, for U.S. Appl. No. 17/866,030, submitted via EFS-Web on Aug. 8, 2024, 9 pages.

Meinhardt, Merve, et al. "Wavelength-dependent penetration depths of ultraviolet radiation in human skin," Journal of Biomedical Optics 2008, 13(4), 044030-1 to 5. (Year: 2008).

"Final Office Action," for U.S. Appl. No. 17/866,023 mailed Nov. 25, 2024 (29 pages).

"Final Office Action," for U.S. Appl. No. 17/866,030 mailed Nov. 6, 2024 (25 pages).

"Response to Non-Final Rejection," mailed on Jul. 8, 2024, for U.S. Appl. No. 17/866,023, submitted via EFS-Web on Oct. 8, 2024, 14 pages.

"Non-Final Office Action," U.S. Appl. No. 17/864,899 mailed Jun. 16, 2025 (38 pages).

"Non-Final Office Action," for U.S. Appl. No. 17/944,582 mailed Jul. 24, 2025, (30 pages).

"Non-Final Office Action," for U.S. Appl. No. 17/866,023 mailed Mar. 27, 2025 (36 pages).

"Non-Final Office Action," for U.S. Appl. No. 17/866,030 mailed May 8, 2025 (33 pages).

"Notice of Allowance," for U.S. Appl. No. 17/866,023 mailed Jul. 21, 2025 (11 pages).

"Response to Final Rejection," mailed on Nov. 6, 2024, for U.S. Appl. No. 17/866,030, submitted via Patent Center on Feb. 6, 2025, 13 pages.

"Response to Non-Final Rejection," mailed on Mar. 27, 2025, for U.S. Appl. No. 17/866,023, submitted via Patent Center on Jun. 27, 2025, 12 pages.

"Response to Non-Final Rejection," mailed on May 8, 2025, for U.S. Appl. No. 17/866,030, submitted via Patent Center on Aug. 6, 2025, 14 pages.

Ashley, Welch "The thermal response of laser irradiated tissue," IEEE Journal of Quantum Electronics, vol. 20, No. 12, pp. 1471-1481, Dec. 1984, doi: 10.1109/JQE.1984.1072339. (11 pages).

Cotler, Howard B., et al. "The Use of Low Level Laser Therapy (LLLT) For Musculoskeletal Pain," MOJ Orthop Rheumatol. 2015;2(5):00068. doi: 10.15406/mojor.2015.02.00068. Epub Jun. 9, 2015. PMID: 26858986; PMCID: PMC4743666. (16 pages).

Henderson, Theodore A, et al. "Near-infrared photonic energy penetration: can infrared phototherapy effectively reach the human brain," Neuropsychiatr Dis Treat. Aug. 21, 2015 ;11:2191-208. doi: 10.2147/NDT.S78182. PM ID: 26346298; PMCID: PMC4552256. (18 pages).

"Response to Non-Final Rejection," mailed on Jul. 24, 2025, for U.S. Appl. No. 17/944,582, submitted via Patent Center on Oct. 22, 2025, 11 pages.

(56)         References Cited

OTHER PUBLICATIONS

"Response to Non-Final Rejection," mailed on Jun. 16, 2025, for U.S. Appl. No. 17/864,899, submitted via Patent Center on Sep. 16, 2025, 12 pages.
"Final Office Action," for U.S. Appl. No. 17/866,030 mailed Nov. 24, 2025 (36 pages).
"Final Office Action," for U.S. Appl. No. 17/944,582 mailed Nov. 20, 2025 (16 pages).

* cited by examiner

| Disease | V/Q Mismatch Cause |
|---|---|
| Heart Failure (reduced cardiac output) | Reduced Perfusion |
| Pulmonary Embolism | |
| Chronic Obstructive Pulmonary Disease (COPD) | Reduced Ventilation |
| Pulmonary Edema (heart failure with normal cardiac output) | |
| Asthma | |
| Pneumonia | |
| Airway Obstruction | |

2700

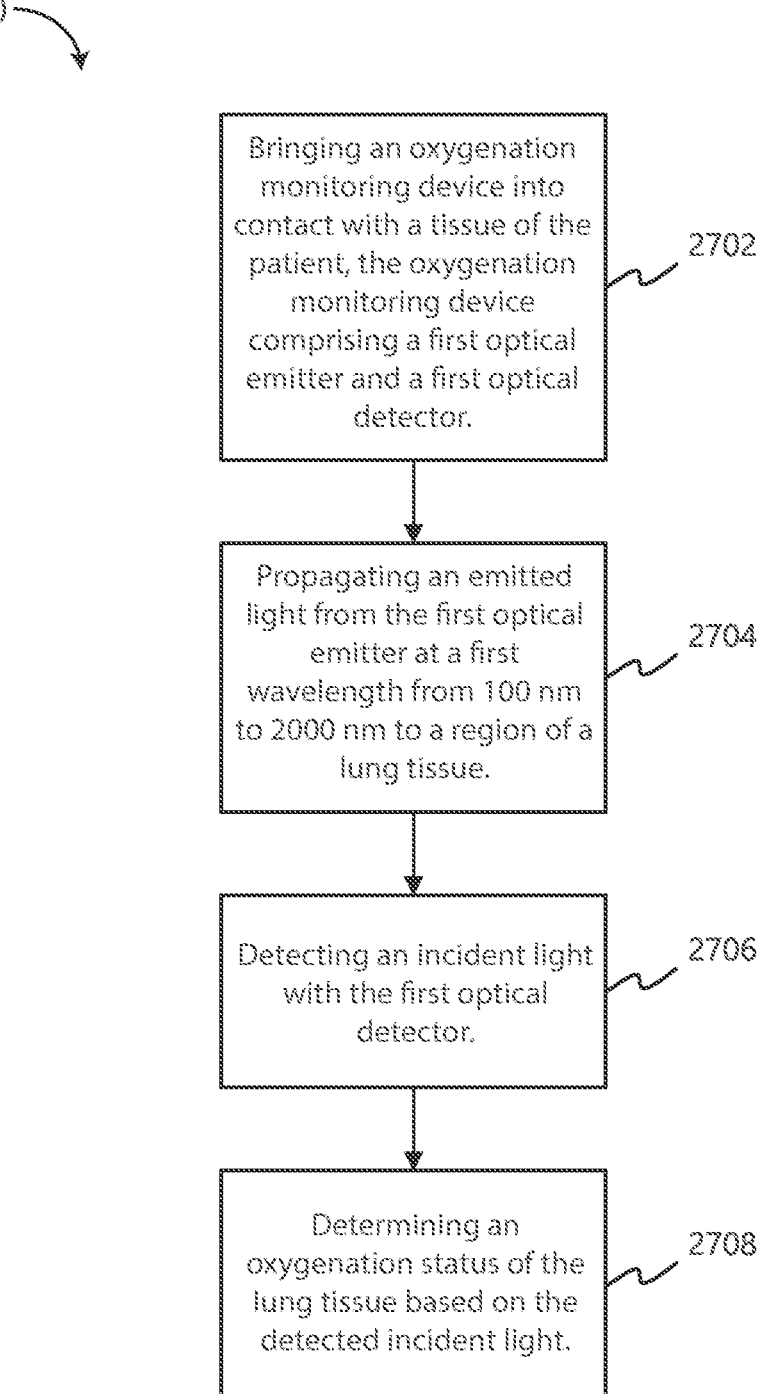

Bringing an oxygenation monitoring device into contact with a tissue of the patient, the oxygenation monitoring device comprising a first optical emitter and a first optical detector.          2702

Propagating an emitted light from the first optical emitter at a first wavelength from 100 nm to 2000 nm to a region of a lung tissue.          2704

Detecting an incident light with the first optical detector.          2706

Determining an oxygenation status of the lung tissue based on the detected incident light.          2708

FIG. 27

DEVICES AND METHODS FOR ASSESSING PULMONARY STATUS USING OPTICAL OXYGENATION SENSING

This application claims the benefit of U.S. Provisional Application No. 63/223,201, filed Jul. 19, 2021, the content of which is herein incorporated by reference in its entirety.

FIELD

Embodiments herein relate to devices and methods for assessing pulmonary status using optical oxygenation sensing. More specifically, embodiments herein relate to devices and methods for assessing pulmonary oxygenation status in lung tissue.

BACKGROUND

Pulmonary status of a patient is a key factor to consider as part of evaluating the overall health of the patient as well as identifying disease states and/or monitoring disease progression. Knowledge of pulmonary status can also be important for tailoring specific therapies to an individual patient.

Peripheral monitoring of blood oxygenation at shallow tissue depths can provide some insight into pulmonary status. However, peripheral monitoring of blood oxygenation at shallow depths may only provide data of questionable accuracy and can be limited by a variety of factors, including low extremity perfusion, vasoconstriction, hypothermia, variation in skin pigmentation, sickle cell anemia, fingernail polish or tattoo ink, motion, ambient light, and the like.

SUMMARY

Embodiments herein relate to devices and methods for assessing pulmonary status using optical oxygenation sensing. In a first aspect, an oxygenation monitoring device can be included having a first optical emitter, wherein the first optical emitter can be configured to emit light at a first wavelength from 100 nanometers (nm) to 2000 nm. The oxygenation monitoring device and further include a first optical detector, wherein the first optical detector can be configured to detect incident light. The device can be configured so that emitted light from the first optical emitter propagates through a lung tissue and detected incident light can be used to determine an oxygenation status of the lung tissue.

In a second aspect, in addition to one or more of the preceding or following aspects, or in the alternative to some aspects, the device can be configured so that emitted light from the first optical emitter propagates through tissue at a depth of at least 1 cm as measured from a surface of the device and/or the first optical emitter and back to the first optical detector.

In a third aspect, in addition to one or more of the preceding or following aspects, or in the alternative to some aspects, the first wavelength can be from 550 nm to 1000 nm.

In a fourth aspect, in addition to one or more of the preceding or following aspects, or in the alternative to some aspects, the first optical emitter and the first optical detector can be spaced along a length of the oxygenation monitoring device from 1 cm to 10 cm apart.

In a fifth aspect, in addition to one or more of the preceding or following aspects, or in the alternative to some aspects, the first wavelength can be from 600 nm to 800 nm.

In a sixth aspect, in addition to one or more of the preceding or following aspects, or in the alternative to some aspects, further can include a second optical emitter, wherein the second optical emitter can be configured to emit light at a second wavelength.

In a seventh aspect, in addition to one or more of the preceding or following aspects, or in the alternative to some aspects, the second wavelength can be from 800 nm to 2000 nm.

In an eighth aspect, in addition to one or more of the preceding or following aspects, or in the alternative to some aspects, emitted light from the first optical emitter can be propagated to a different depth than emitted light from the second optical emitter.

In a ninth aspect, in addition to one or more of the preceding or following aspects, or in the alternative to some aspects, oxygenation status of the lung tissue can be indicative of a pulmonary ventilation or perfusion status.

In a tenth aspect, in addition to one or more of the preceding or following aspects, or in the alternative to some aspects, the device can be further configured to monitor a progression or regression of one or more conditions can include chronic obstructive pulmonary disease (COPD), pulmonary edema, asthma, pneumonia, airway obstruction, heart failure, acute respiratory distress syndrome (ARDS), septic shock, or pulmonary embolism.

In an eleventh aspect, in addition to one or more of the preceding or following aspects, or in the alternative to some aspects, the device can be further configured to determine one of a heart rate, a respiratory rate, a tidal volume, or an extravascular lung water concentration.

In a twelfth aspect, in addition to one or more of the preceding or following aspects, or in the alternative to some aspects, the device can further include a housing, and a flexible member, wherein the flexible member can be connected to the housing and extends in a direction away from the housing.

In a thirteenth aspect, in addition to one or more of the preceding or following aspects, or in the alternative to some aspects, the flexible member can be from 1 centimeters (cm) to 3 cm in length.

In a fourteenth aspect, in addition to one or more of the preceding or following aspects, or in the alternative to some aspects, the first optical emitter can be disposed along a length of the flexible member.

In a fifteenth aspect, in addition to one or more of the preceding or following aspects, or in the alternative to some aspects, the optical detector can be disposed along a length of the flexible member.

In a sixteenth aspect, in addition to one or more of the preceding or following aspects, or in the alternative to some aspects, the first optical emitter and the optical detector can be both disposed along a length of the flexible member.

In a seventeenth aspect, in addition to one or more of the preceding or following aspects, or in the alternative to some aspects, the first optical emitter and the optical detector can be spaced along a planer surface of from 1 cm to 10 cm apart.

In an eighteenth aspect, in addition to one or more of the preceding or following aspects, or in the alternative to some aspects, wherein propagation of the emitted light through a lung tissue includes propagation of the emitted light from 1 cm to 5 cm in depth as measured from a surface of the oxygenation monitoring device.

In a nineteenth aspect, in addition to one or more of the preceding or following aspects, or in the alternative to some aspects, the oxygenation monitoring device can be an implantable device.

In a twentieth aspect, in addition to one or more of the preceding or following aspects, or in the alternative to some aspects, the oxygenation monitoring device can be a wearable device.

In a twenty-first aspect, in addition to one or more of the preceding or following aspects, or in the alternative to some aspects, further can include a measurement circuit configured to control operation of the first optical emitter and the optical detector.

In a twenty-second aspect, a method for measuring an oxygenation status in a patient can be included, the method including bringing an oxygenation monitoring device into contact with a tissue of the patient, the oxygenation monitoring device can include an optical sensor can include a first optical emitter and an optical detector, propagating an emitted light from the first optical emitter at a first wavelength from 100 nanometers (nm) to 2000 nm to a region of a lung tissue, detecting an incident light with the optical detector, determining an oxygenation status of the lung tissue based on the detected incident light, wherein determining the oxygenation status includes performing a ratiometric calculation using at least one of a measured absorption, light scattering or phase.

In a twenty-third aspect, in addition to one or more of the preceding or following aspects, or in the alternative to some aspects, the optical sensor further includes a second optical emitter configured to emit light at a second wavelength different than the first wavelength, and wherein the ratiometric calculation can be based on detecting incident light from the first optical emitter and second optical emitter.

In a twenty-fourth aspect, in addition to one or more of the preceding or following aspects, or in the alternative to some aspects, the method can further include implanting the oxygenation monitoring device subcutaneously at or near a site of a lung tissue so that the first light emitter and the first light detector can be directed toward an interior of the patient toward a surface of the lung tissue.

In a twenty-fifth aspect, in addition to one or more of the preceding or following aspects, or in the alternative to some aspects, the site can be chosen based on whether the patient is likely to experience reduced ventilation or reduced perfusion.

In a twenty-sixth aspect, in addition to one or more of the preceding or following aspects, or in the alternative to some aspects, the site can include an upper portion of the lungs or a lower portion of the lungs.

In a twenty-seventh aspect, in addition to one or more of the preceding or following aspects, or in the alternative to some aspects, the emitted light can be propagated at a depth of from 1 cm to 5 cm into the lung tissue.

In a twenty-eighth aspect, in addition to one or more of the preceding or following aspects, or in the alternative to some aspects, wherein determining the oxygenation status of the lung tissue can include measuring at least one physical property of a lung tissue can include extravascular lung water, airway constriction, airway mucous, and airway inflammation.

In a twenty-ninth aspect, in addition to one or more of the preceding or following aspects, or in the alternative to some aspects, the method can further include monitoring a progression or regression of one or more conditions can include chronic obstructive pulmonary disease (COPD), pulmonary edema, asthma, pneumonia, airway obstruction, heart failure, acute respiratory distress syndrome (ARDS), septic shock, or pulmonary embolism.

In a thirtieth aspect, in addition to one or more of the preceding or following aspects, or in the alternative to some aspects, the method can further include measuring one or more of a heart rate, a respiratory rate, a tidal volume, circadian rhythm, posture, or an extravascular lung water concentration.

In a thirty-first aspect, in addition to one or more of the preceding or following aspects, or in the alternative to some aspects, wherein measuring one or more of a heart rate, a respiratory rate, a tidal volume, circadian rhythm, posture, or an extravascular lung water concentration can be further used to determine or interpret the oxygenation status.

In a thirty-second aspect, in addition to one or more of the preceding or following aspects, or in the alternative to some aspects, the method can further include measuring at least one of absorption, light scattering, or phase with the optical detector.

In a thirty-third aspect, in addition to one or more of the preceding or following aspects, or in the alternative to some aspects, the method can further include creating a composite score using at least two of the measured absorption, light scattering, or phase.

In a thirty-fourth aspect, in addition to one or more of the preceding or following aspects, or in the alternative to some aspects, the method can further include calculating an AC signal component and a DC signal component of the detected incident light to determine the oxygenation status of the lung tissue.

In a thirty-fifth aspect, in addition to one or more of the preceding or following aspects, or in the alternative to some aspects, the AC signal component and the DC signal component can be used for determining a ratio of ratios between the ratio of an AC signal component to a DC signal component at a first wavelength to the ratio of an AC signal component to a DC signal component at a second wavelength.

In a thirty-sixth aspect, in addition to one or more of the preceding or following aspects, or in the alternative to some aspects, the AC signal component and the DC signal component can be used for determining a ratio of ratios between the ratio of an AC signal component to a DC signal component at a first depth to the ratio of an AC signal component to a DC signal component at a second depth.

In a thirty-seventh aspect, in addition to one or more of the preceding or following aspects, or in the alternative to some aspects, the method can further include providing a therapy to the patient upon determining an oxygenation status of the lung tissue.

In a thirty-eighth aspect, a sensor system for detecting an oxygenation status of a patient can be included having a first oxygenation status monitoring device, the first oxygenation status monitoring device can include a first optical emitter, wherein the first optical emitter can be configured to emit light at a first wavelength from 100 nm to 2000 nm, and a first optical detector, wherein the first optical detector can be configured to detect incident light, at least one secondary sensor can include a pulse oximetry sensor, a chemical sensor, a posture sensor, or a heart rate sensor, wherein the light from the first optical emitter can be configured to propagate through a lung tissue, and wherein the detected incident light and secondary sensor data can be used to determine an oxygenation status of the lung tissue.

In a thirty-ninth aspect, in addition to one or more of the preceding or following aspects, or in the alternative to some aspects, wherein determining the oxygenation status includes performing a ratiometric calculation using at least one of a measured absorption, light scattering or phase.

In a fortieth aspect, in addition to one or more of the preceding or following aspects, or in the alternative to some aspects, further can include a therapy interface configured to deliver a therapy to the patient after determining the oxygenation status of the lung tissue.

In a forty-first aspect, in addition to one or more of the preceding or following aspects, or in the alternative to some aspects, wherein at least one of the oxygenation status monitoring device or the secondary sensor can be implantable.

In a forty-second aspect, in addition to one or more of the preceding or following aspects, or in the alternative to some aspects, the system can further include a second oxygenation status monitoring device, the second oxygenation status monitoring device can include a second optical emitter, wherein the second optical emitter can be configured to emit light at a second wavelength, and a second optical detector, wherein the second optical detector can be configured to detect incident light.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE FIGURES

Aspects may be more completely understood in connection with the following figures (FIGS.), in which:

FIG. 27 is a flow diagram of a method in accordance with various embodiments herein.

Figure 1:
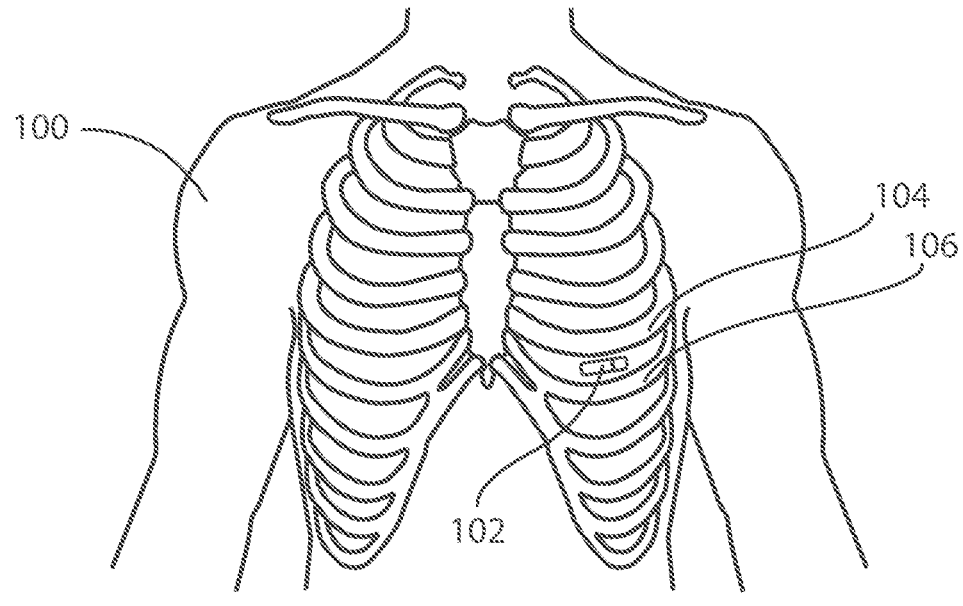
FIG. 1 is a schematic view of an implanted oxygenation monitoring device in accordance with the embodiments herein.

While embodiments are susceptible to various modifications and alternative forms, specifics thereof have been shown by way of example and drawings, and will be described in detail. It should be understood, however, that the scope herein is not limited to the particular aspects described. On the contrary, the intention is to cover modifications, equivalents, and alternatives falling within the spirit and scope herein.

DETAILED DESCRIPTION

Embodiments herein relate to devices and methods for assessing pulmonary status using optical oxygenation sensing. More specifically, embodiments herein relate to devices and methods for assessing pulmonary oxygenation status in lung tissue. As described above, peripheral monitoring of blood oxygenation status can be limited due to various factors and is typically limited to shallow tissue depths of under one centimeter (cm). However, systems, devices, and methods herein are directed to determining and assessing pulmonary oxygenation status using optical sensing that can penetrate deeply into tissues, such as pulmonary tissue, at depths of greater than one centimeter into the tissue.

Without being bound by theory, tissue oxygenation can be determined by measuring the absorption of oxygenated hemoglobin (i.e., oxyhemoglobin—Hb) and deoxygenated hemoglobin (i.e., deoxyhemoglobin—HbO₂) in the blood using optical oxygenation sensing techniques. Hemoglobin is a protein molecule found in red blood cells that contains two alpha and two beta subunits that each surround a central heme group. Each heme group contains iron that can bind one oxygen molecule per heme such that each molecule of hemoglobin can bind up to four oxygen molecules. Oxygen saturation is the ratio of the statistical average of oxygenated hemoglobin concentration to the total hemoglobin concentration (both oxyhemoglobin and deoxyhemoglobin) in the blood according to the following equation:

$$SpO_2 = \frac{HbO_2}{(HbO_2 + Hb)}$$

Assessing pulmonary status within lung tissue using optical oxygenation sensing can be achieved by using light reflectance through deep tissues of the body. Light emitted from an optical emitter of an oxygenation monitoring device can propagate deeply into a patient's tissues and back to the oxygenation monitoring device and detected by an optical detector. As light travels through the tissues of a patient, it can be affected by various optical properties including transmittance, reflectance, absorption, light attenuation, scatting, wavelength, current, and fluorescence. Devices and systems herein can be configured to utilize the optical properties of light having passed through deep tissue to sensing physiological parameters such as pulmonary oxygenation at significant internal depths within a patient, such as where the depth is greater than one centimeter. The devices herein can be configured to cause light to penetrate deeply into the tissue by optimizing emitter-detector spacing, wavelength selection, and/or the use of multiple wavelengths.

Devices and/or systems herein can take the form of implantable devices, wearable devices, or a combination of both. By way of example, devices and/or systems herein can include oxygenation monitoring devices that include implantable oxygenation monitoring devices, wearable oxygenation monitoring devices, or a combination of both types of devices. Referring now to FIG. 1, a schematic view of an implantable oxygenation monitoring device is shown in accordance with various embodiments herein. The oxygenation monitoring device 102 is shown in FIG. 1 as being positioned between the left fifth rib 104 and the left sixth rib 106 within the left fifth intercostal space of patient 100. While placement of the oxygenation monitoring device 102 is shown within the left fifth intercostal space, it will be appreciated that the oxygenation monitoring device 102 can be implanted within other locations of the body and, in particular, in or adjacent to other intercostal spaces along either the right side or the left side of a patient's rib cage or in anterior, lateral, posterior, superior, or inferior thoracic locations.

The implantation depth of the oxygenation monitoring device can include implantation depths of from 1 millimeter (mm) to 25 mm or more below the skin layer of a patient's body. In some embodiments, the implantation depth below the skin layer can be greater than or equal to 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, 26 mm, 27 mm, 28 mm, 29 mm, or 30 mm, or can be an amount falling within a range between any of the foregoing.

The implantation depth can be tailored to provide an oxygenation monitoring device to lung distance of from 1 mm to 45 mm or more. In some embodiments, the distance between the oxygenation monitoring device and lung can be greater than or equal to 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, 26 mm, 27 mm, 28 mm, 29 mm, 30 mm, 31 mm, 32 mm, 33 mm, 34 mm, 35 mm, 36 mm, 37 mm, 38 mm, 39 mm, 40 mm 41 mm, 42 mm, 43 mm, 44 mm, or 45 mm, or can be an amount falling within a range between any of the foregoing.

In some scenarios, the implantable oxygenation monitoring devices embodied herein can be used in combination with various types of implantable monitoring devices, such as implantable cardiac monitors, and/or implantable therapeutic devices, including, but not limited to, implantable cardiac rhythm management devices, implantable pacemakers, implantable cardioverter-defibrillator devices, and the like. The implantable therapeutic and/or monitoring devices can be implanted along with the oxygenation monitoring devices described herein. In other embodiments, the implantable oxygenation monitoring device can be included within an implantable therapeutic device.

Figure 2:
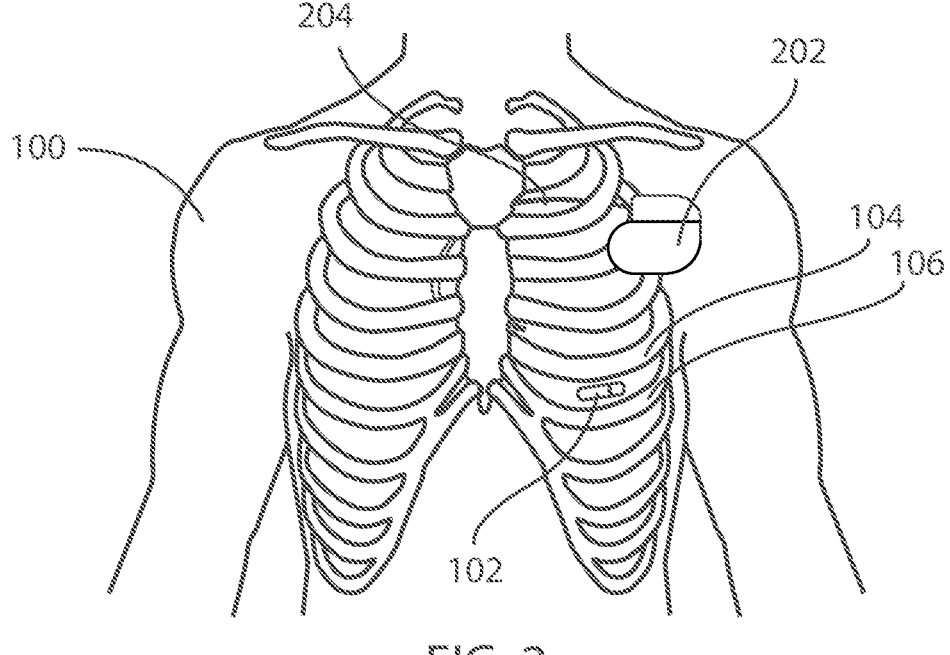
FIG. 2 is a schematic view of an implanted oxygenation monitoring device system in accordance with the embodiments herein.

Referring now to FIG. 2, a schematic view of an implantable oxygenation monitoring device is shown in accordance with various embodiments herein. The oxygenation monitoring device 102 is shown in FIG. 2 as being positioned between the left fifth rib 104 and the left sixth rib 106 within the left fifth intercostal space of patient 100. FIG. 2 further includes an implantable therapeutic device 202 positioned within the chest of the patient 100. Implantable therapeutic device 202 can be implanted at any position within patient 100 to provide a desired therapy to the patient in conjunction with signals determined by the oxygenation monitoring device, as will be discussed elsewhere herein. Implantable therapeutic device 202 can include one or more electrical stimulation leads 204 placed within the body of patient 100 at or near a treatment site.

Figure 3:
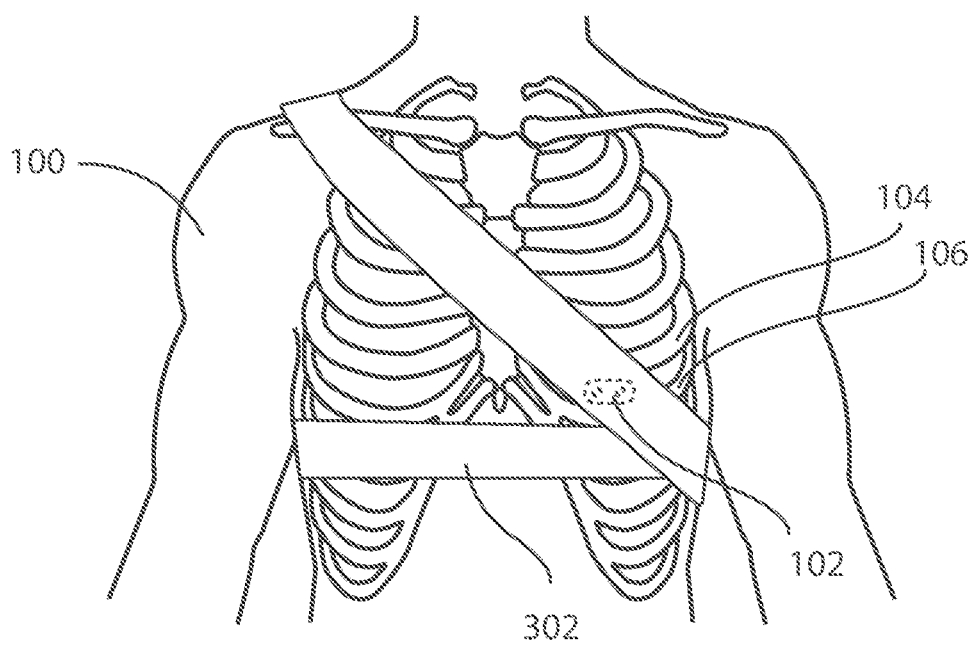
FIG. 3 is a schematic view of a wearable oxygenation monitoring device in accordance with the embodiments herein.

As referenced above, oxygenation monitoring devices herein can include those that are wearable devices. Referring now to FIG. 3, a schematic view of a wearable oxygenation monitoring device is shown in accordance with various embodiments herein. The oxygenation monitoring device 102 can be disposed along a length of a wearable strap 302 and externally positioned between the left fifth rib 104 and the left sixth rib 106 over the left fifth intercostal space of patient 100. While placement of the oxygenation monitoring device 102 is shown placed over the left fifth intercostal space, it will be appreciated that the oxygenation monitoring device 102 can also be positioned over or adjacent to other intercostal spaces along either the right side or the left side of a patient's rib cage.

Figure 4:
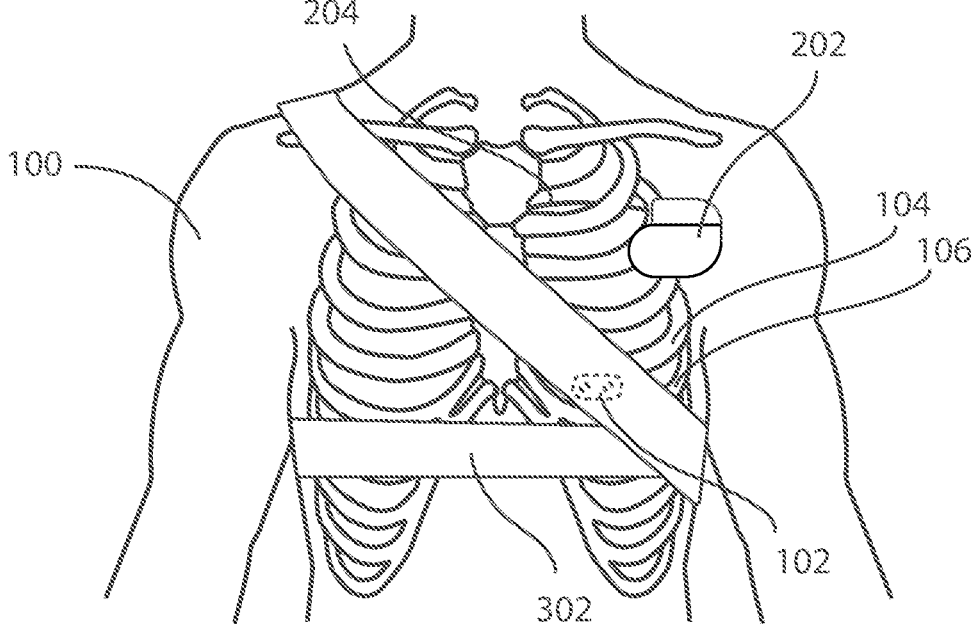
FIG. 4 is a schematic top view of a wearable oxygenation monitoring device system in accordance with the embodiments herein.

The wearable oxygenation monitoring devices embodied herein can be used in combination with various types of implantable therapeutic devices, such as those described above. The implantable therapeutic devices can be implanted and used in a system in conjunction with the wearable oxygenation monitoring devices described herein. Referring now to FIG. 4, a schematic view of a wearable oxygenation monitoring device is shown in accordance with various embodiments herein. The wearable oxygenation monitoring device 102 can be disposed along a length of a wearable strap 302 and externally positioned between the left fifth rib 104 and the left sixth rib 106 over the left fifth intercostal space of patient 100 or at another site. FIG. 4 further includes an implantable therapeutic device 202 positioned within the chest of the patient 100. Implantable therapeutic device 202 can be implanted at any position within patient 100 to provide a desired therapy to the patient in conjunction with signals determined by the oxygenation monitoring device, as discussed elsewhere herein. Implantable therapeutic device 202 can include one or more electrical stimulation leads 204 placed within the body of patient 100 at or near a treatment site. In some embodiments, the wearable oxygenation monitoring devices herein can be or include a patch sensor temporarily affixed to a patient by an adhesive, or it can be a garment worn on the body of a patient.

Figure 5:
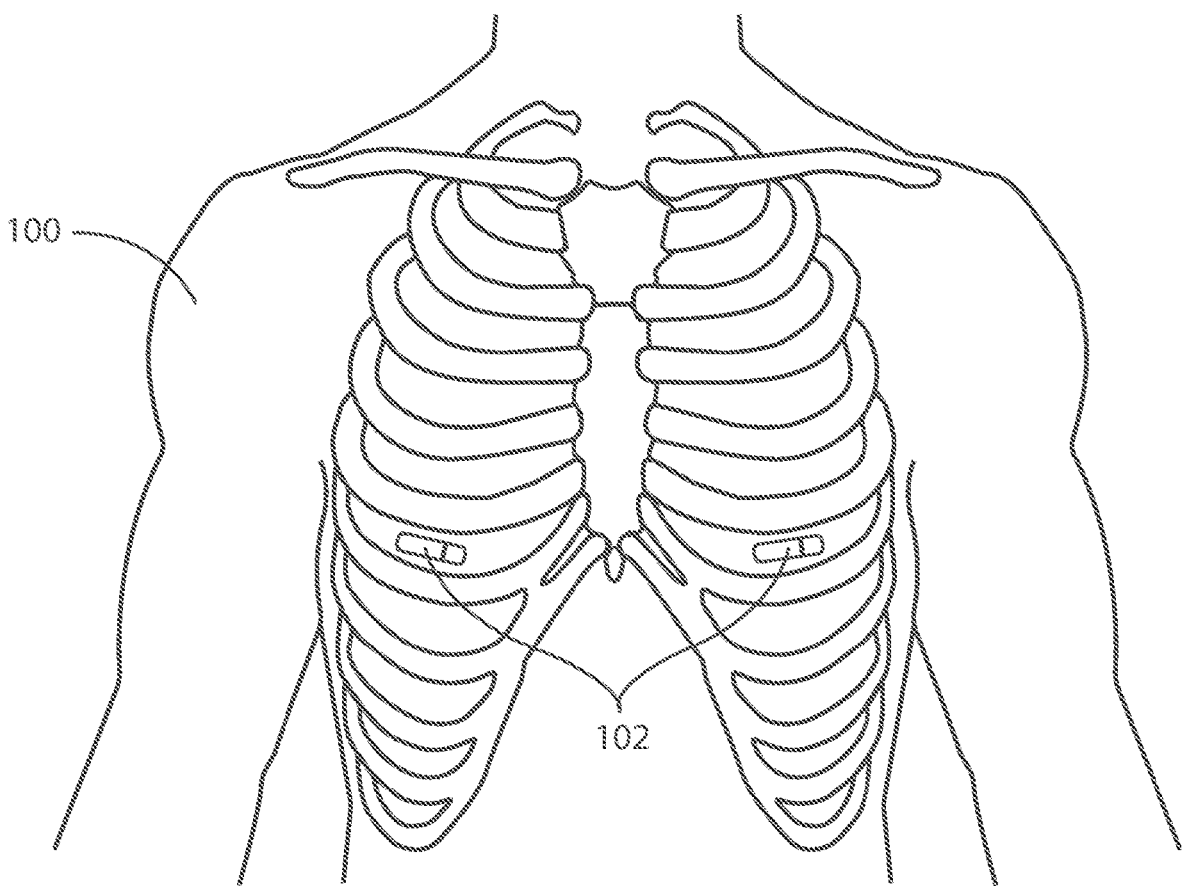
FIG. 5 is a schematic view of a system including multiple implanted oxygenation monitoring devices in accordance with the embodiments herein.

In some embodiments only a single oxygenation monitoring device may be implanted while in other embodiments multiple oxygenation monitoring devices can be implanted within a patient. Referring now to FIG. 5, a schematic view of a system with multiple implantable oxygenation monitoring devices is shown in accordance with various embodiments herein. The oxygenation monitoring devices 102 are shown in FIG. 5 as being positioned between the fifth rib and the sixth rib within the left fifth intercostal space and right firth intercostal space, respectively. While placement of the oxygenation monitoring devices 102 are shown within the left fifth intercostal space and right fifth intercostal space, it will be appreciated that the oxygenation monitoring devices 102 can be placed within a combination of intercostal spaces along either the right side or the left side of a patient's rib cage or at other sites.

While FIG. 5 shows a combination of two oxygenation monitoring devices implanted within the intercostal spaces of patient 100, it will be appreciated that more than two oxygenation monitoring devices can be implanted within patient 100. In some embodiments, two, three, four, or five oxygenation monitoring devices can be implanted within patient 100. In other embodiments, more than five oxygenation monitoring devices can be implanted within patient 100. In an embodiment, one or more of the oxygen monitoring device can be implanted and one or more of the oxygen monitoring device can be wearable.

The oxygenation monitoring devices herein can be configured to determine an oxygenation status of a lung tissue. In various embodiments, the oxygenation monitoring devices herein can be further configured to monitor a progression or regression of one or more conditions comprising chronic obstructive pulmonary disease (COPD), pulmonary edema, asthma, pneumonia, airway obstruction, heart failure, acute respiratory distress syndrome (ARDS), septic shock, or pulmonary embolism. In other embodiments, the oxygenation monitoring devices herein can be further configured to determine one or more of a heart rate, a respiratory rate, a tidal volume, or an extravascular lung water concentration, as discussed elsewhere herein.

In various embodiments, oxygenation monitoring devices can be implanted along with at least one secondary sensor. Secondary sensors can include, but are not to be limited to, a pulse oximetry sensor, a chemical sensor, a posture sensor, or a heart rate sensor. The secondary sensors can be used to determine one or more of a heart rate, a respiratory rate, a tidal volume, or an extravascular lung water concentration. It will be appreciated that in various embodiments, the optical emitters and optical detectors can be disposed together on the same side of the oxygenation monitoring device, while the secondary sensors can be disposed on the opposite side of the oxygenation monitoring device. In other embodiments, the optical emitters, optical detectors, and secondary sensors can be disposed together on the same side of the oxygenation monitoring device.

The oxygenation monitoring devices herein can include various components, such as optical emitters, optical detectors, secondary sensors, and optical barriers in various configurations in accordance with the embodiments herein and as shown and described in reference to FIGS. 6-13.

Figure 6:
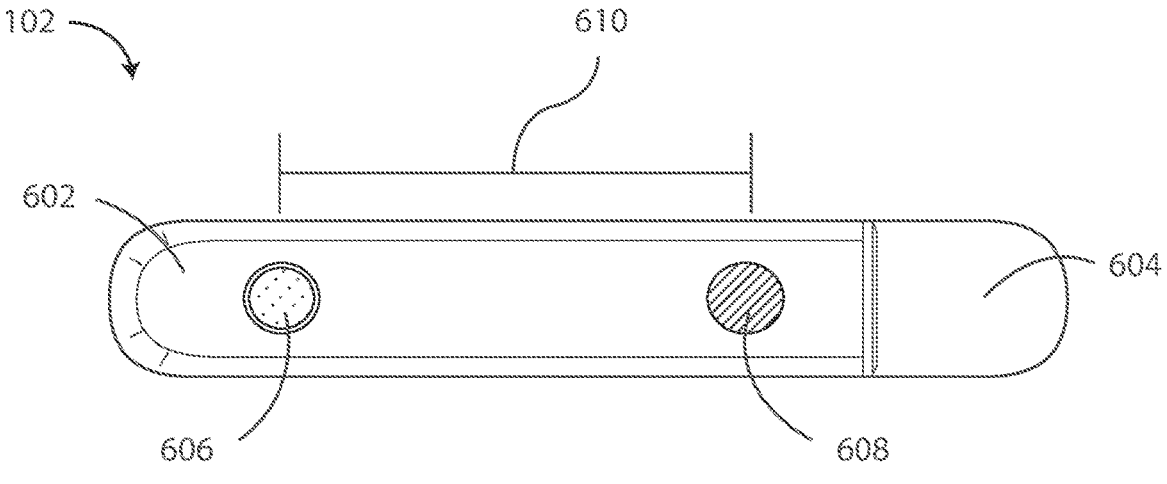
FIG. 6 is a schematic top view of an oxygenation monitoring device in accordance with various embodiments herein.

Referring now to FIG. 6, an oxygenation monitoring device 102 is shown in accordance with the embodiments herein. In this embodiment, the oxygenation monitoring device 102 can include a housing 602 and a header 604 coupled to the housing 602. Various materials can be used to form the housing 602 and the header 604. In some embodiments, the housing 602 can be formed of a material such as a metal, ceramic, a polymer, or a composite. The header 604 can be formed of various materials, and in some embodiments the header 604 can be formed of a translucent polymer such as an epoxy material. In some embodiments the header 604 can be hollow. In other embodiments the header 604 can be filled with components and/or structural materials such as epoxy or another material such that it is non-hollow. In yet other embodiments, the oxygenation monitoring device 102 can be devoid of a header 604 or can include a header at either end or both ends of the oxygenation monitoring device. In an embodiment part of all of the housing 602 can be transparent to provide a window for optical components of oxygenation monitoring device 102.

In various embodiments, the oxygenation monitoring device 102 can include a first optical emitter 606 and a first optical detector 608, each coupled to the housing 602. The first optical emitter 606 can be configured to emit light at a first wavelength of from 100 nanometers (nm) to 2000 nm. In various embodiments, the first optical emitter can be configured to emit light at a first wavelength of from 550 nm to 1000 nm. In some embodiments, the first optical emitter can be configured to emit light at a first wavelength of from 600 nm to 800 nm. In various embodiments, the first optical emitter 606 can be configured to emit light at a first wavelength that can be greater than or equal to 100 nm, 200 nm, 300 nm, 400 nm, 500 nm, 600 nm, 700 nm, 800 nm, 900 nm, 1000 nm, 1100 nm, 1200 nm, 1300 nm, 1400 nm, 1500 nm, 1600 nm, 1700 nm, 1800 nm, 1900 nm, or 2000 nm, or can be any wavelength falling within a range between any of the foregoing.

The first optical detector 608 can be configured to detect incident light originating from one or more optical emitters, such as the first optical emitter 606. The first optical detector 608 can be configured to detect light after it has propagated into the tissue of a patient to a given depth from the first optical emitter 606 and back to the first optical detector 608. For example, the oxygenation monitoring device 102 can be configured to provide for the propagation of the emitted light through a lung tissue such that propagation of the emitted light occurs from about 1 centimeter (cm) in depth to 5 cm in depth as measured from a surface of the oxygenation monitoring device 102 to a target tissue. In some embodiments, the depth or propagation of the emitter light can be greater than or equal to 1 cm, 2 cm, 3 cm, 4 cm, or 5 cm, or can be an amount falling within a range between any of the foregoing. In various embodiments, the configuration of the oxygenation monitoring device 102 can allow for the propagation of the emitted light through a lung tissue when a surface of the oxygenation monitoring device 102 is directed to the interior of a patient's body toward the surface of the lung tissue. The detected incident light can be used to determine an oxygenation status of lung tissue within a patient, as will be discussed elsewhere herein.

It will be appreciated that first optical emitter 606 and first optical detector 608 can be positioned at any location along oxygenation monitoring device 102 to achieve optimal propagation of light into the tissue of a patient. The first optical emitter 606 and first optical detector 608 can be spaced along a length of the oxygenation monitoring device 102 at a distance 610 from 1 cm to 10 cm apart. In some embodiments, a distance 610 between the first optical emitter and the first optical detector can be greater than or equal to 1 cm, 2 cm, 3 cm, 4 cm, 5 cm, 6 cm, 7 cm, 8 cm, 9 cm, 10 cm, 11 cm, 12 cm, 13 cm, 14 cm, or 15 cm, or can be an amount falling within a range between any of the foregoing. In various embodiments, the first optical emitter and the first optical detector are spaced along a planer surface of the oxygenation monitoring device of from 1 cm to 10 cm apart.

The oxygenation monitoring device 102 can take on various dimensions in the length, width, and thickness directions. In a particular embodiment herein, it can be approximately 5 to 10 cm in length, 1 cm to 1.5 cm wide, and 0.25 cm to 1.0 cm thick. In some embodiments, the length of oxygenation monitoring device 102 can be greater than or equal to 1 cm, 2 cm, 3 cm, 4 cm, 5 cm, 6 cm, 7 cm, 8 cm, 9 cm, 10 cm, 11 cm, 12 cm, 13 cm, 14 cm, or 15 cm, or can be an amount falling within a range between any of the foregoing. In some embodiments, the oxygenation monitoring device 102 can be about 0.25 cm, 0.5 cm, 0.75 cm, 1.0 cm, or 2.0 cm in width. In some embodiments the width can be in a range wherein any of the foregoing widths can serve as the upper or lower bound of the range, provided that the upper bound is greater than the lower bound. In some embodiments, the oxygenation monitoring device 102 can be about 0.25 cm, 0.50 cm, 0.75 cm or 1.0 cm, 1.25 cm, 1.50 cm, 1.75 cm, 2.0 cm, 2.25 cm, 2.50 cm, or 3.0 cm thick, or can be an amount falling within a range between any of the foregoing. In some embodiments the thickness can be in a range wherein any of the foregoing thicknesses can serve as the upper or lower bound of the range, provided that the upper bound is greater than the lower bound.

Figure 7:
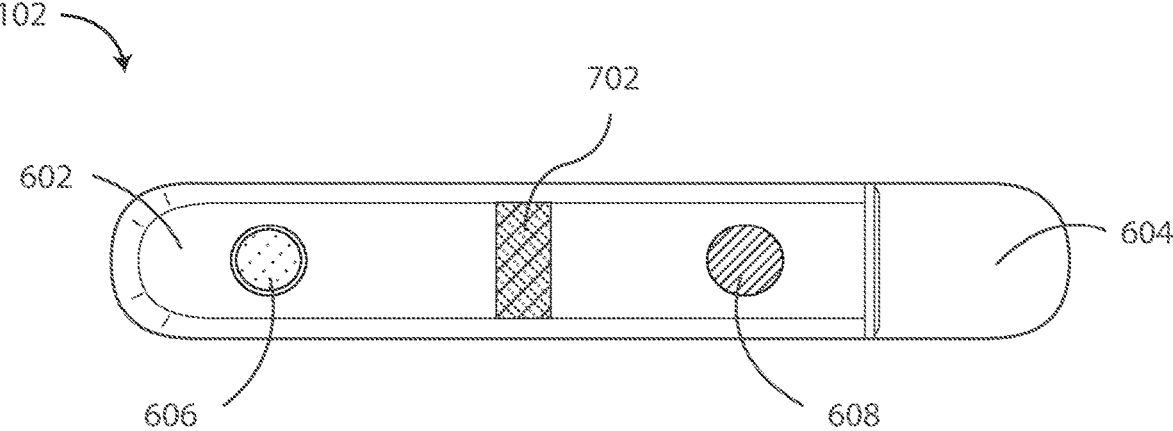
FIG. 7 is a schematic top view of an oxygenation monitoring device in accordance with various embodiments herein.

In various embodiments, the oxygenation monitoring devices herein can include an optical barrier device disposed between the optical emitters and optical detectors to prevent a direct path for light emitted from an optical emitter to an optical detector. Referring now to FIG. 7, an oxygenation monitoring device 102 is shown in accordance with the embodiments herein. The oxygenation monitoring device 102 can include the features of the oxygenation monitoring device 102 of FIG. 6, and can further include an optical barrier device 702 disposed in between the first optical emitter 606 and the first optical detector 608. In some embodiments, the optical barrier device 702 can be mounted on the surface of the oxygenation monitoring device 102. The optical barrier device 702 can include various materials including light blocking materials such as opaque compositions and materials, polymers, metals, dyed materials, and the like.

Figures 8, 9:
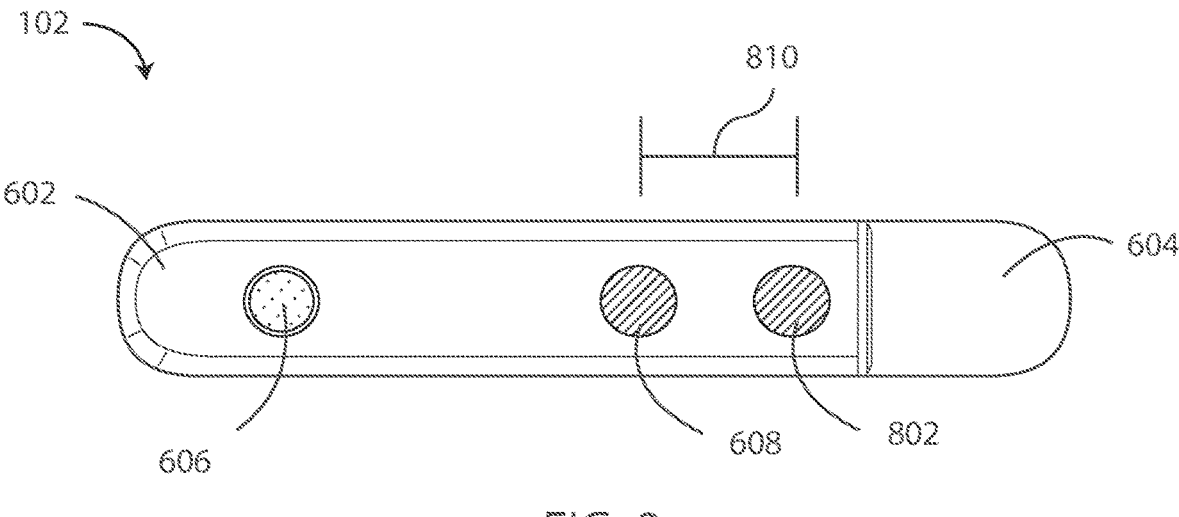
FIG. 8 is a schematic top view of an oxygenation monitoring device in accordance with various embodiments herein.
FIG. 9 is a schematic top view of an oxygenation monitoring device in accordance with various embodiments herein.

It will be appreciated that the oxygenation monitoring devices embodied herein can include various configurations of multiple optical emitters or optical detectors disposed along a length of the oxygenation monitoring devices. Referring now to FIG. 8, an oxygenation monitoring device 102 is shown in accordance with the embodiments herein. The oxygenation monitoring device 102 can include a housing 602 and a header 604 coupled to the housing 602.

The oxygenation monitoring device 102 can include a first optical emitter 606, a first optical detector 608, and a second optical detector 802, each coupled to the housing 602. The first optical emitter 606 and first optical detector 608 can be spaced along a length of the oxygenation monitoring device 102 as discussed in reference to FIG. 6. The first optical detector 608 and the second optical detector 802 can be disposed along a length of the oxygenation monitoring device 102 at a distance 810 of from 1 cm to 5 cm or more apart. The second optical detector 802 can be configured to detect incident light. In some embodiments, the distance 810 between the first optical detector and the second optical detector can be greater than or equal to 0.25 cm, 0.5 cm, 1 cm, 2 cm, 3 cm, 4 cm, 5 cm, or more, or can be an amount falling within a range between any of the foregoing. Subject to other factors, the greater distance 610 the greater the depth of propagation of light through the tissue.

Referring now to FIG. 9, an oxygenation monitoring device 102 is shown in accordance with the embodiments herein. The oxygenation monitoring device 102 can include a housing 602 and a header 604 coupled to the housing 602. The oxygenation monitoring device 102 can include a first optical emitter 606, a second optical emitter 906, and first optical detector 608, each coupled to the housing 602. The first optical emitter 606 and first optical detector 608 can be spaced along a length of the oxygenation monitoring device 102 as discussed in reference to FIG. 6. The first optical emitter 606 and the second optical emitter 906 can be disposed along a length of the oxygenation monitoring device 102 at a distance 910 of from 1 cm to 5 cm or more apart. In some embodiments, the distance 910 between the first optical emitter and the second optical emitter can be greater than or equal to 0.25 cm, 0.5 cm, 1 cm, 2 cm, 3 cm, 4 cm, or 5 cm, or more, or can be an amount falling within a range between any of the foregoing. It will be appreciated, however, that the depth of propagation of light through tissue is dependent on the distance between the emitter and the detector and not the distance between the emitters.

The second optical emitter 906 can be configured to emit light at a second wavelength when present on an oxygenation monitoring device with a first optical emitter. In various embodiments, the second optical emitter 906 can be configured to emit light at a second wavelength different than the first wavelength emitted from the first optical emitter 606. In some embodiments, the second optical emitter can be configured to emit light at a second wavelength of from 800 nm to 2000 nm. In various embodiments, the first optical emitter 606 can be configured to emit light at a second wavelength that can be greater than or equal to 800 nm, 900 nm, 1000 nm, 1100 nm, 1200 nm, 1300 nm, 1400 nm, 1500 nm, 1600 nm, 1700 nm, 1800 nm, 1900 nm, or 2000 nm, or can be an amount falling within a range between any of the foregoing.

It will be appreciated that optical emitters herein can be used substantially continuously or only during certain time periods. For example, in some cases, the device and/or system can be configured to measure oxygenation continuously or substantially continuously. In such a scenario, an optical emitter can be turned on continuously or intermittently as part of a duty cycle such as a certain fraction of time that the emitter is emitting light. It will be appreciated, however, that continuous operation of an emitter may consume substantial energy and lower the battery life of an implanted device. Thus, as a further example, in some embodiments, the device or system can evaluate oxygenation only during certain periods of time. For example, the device or system can evaluate oxygenation only when it receives a command to measure oxygenation coming from a different device or from a clinician or other system user. As another example, the device or system can evaluate oxygenation according to a preset schedule. As another example, the device or system can evaluate oxygenation after detecting a particular occurrence or event using one or more sensors, such as an abnormal heart rhythm, an abnormal respiration pattern, or the like. In scenarios where there is more than one emitter, the emitters can be turned on simultaneously or in an alternating pattern. It will be appreciated that the optical emitters and optical detectors can be formed from various materials. Optical emitters can include a light source such as a light emitting diode (LED), vertical-cavity surface-emitting lasers (VCSELs), electroluminescent (EL) devices, and the like. Optical detectors can include a component selected from the group including of a photo-diode, a phototransistor, a charge-coupled device (CCD), a junction field effect transistor (JFET) optical sensor, a complementary metal-oxide semiconductor (CMOS) optical sensor, an integrated photo detector integrated circuit, a light to voltage converter, and the like. Optical emitters and optical detectors are discussed in further detail below.

Figure 10:
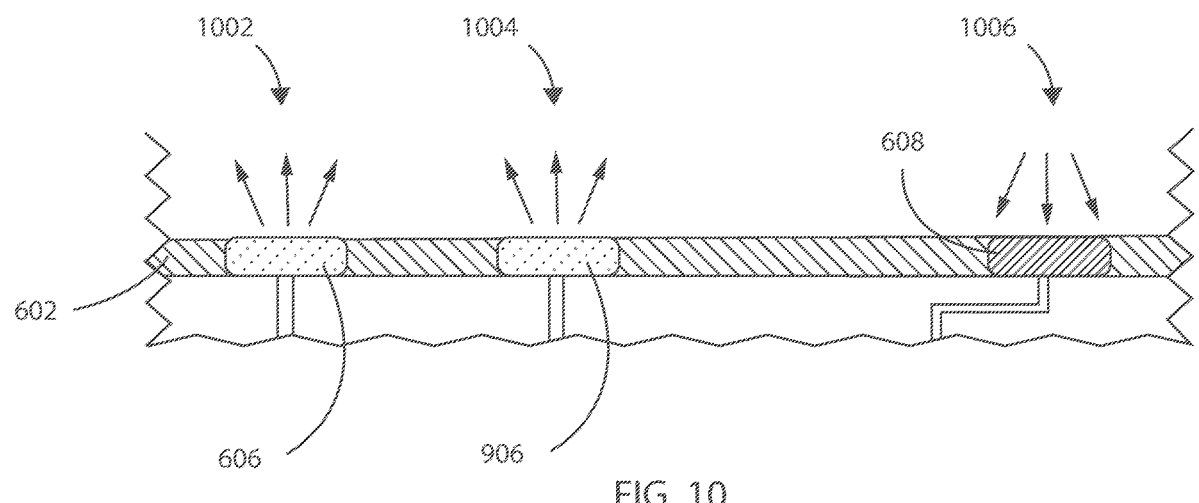
FIG. 10 is a schematic cross-sectional view of an oxygenation monitoring device along line 10-10' of FIG. 9 in accordance with various embodiments herein.

Referring now to FIG. 10, a cross-sectional view of an oxygenation monitoring device is shown in accordance with various embodiments herein. Oxygenation monitoring device 102 includes housing 602 having a first optical emitter 606, a second optical emitter 906, and a first optical detector 608. The first optical emitter 606 can be configured to emit light at a first wavelength 1002 from 100 nm to 2000 nm. The second optical emitter 906 can be configured to emit light at a second wavelength 1004 from 800 nm to 2000 nm. In various embodiments, the emitted light of a first wavelength from the first optical emitter can be propagated to a different depth than the emitted light of a second wavelength from the second optical emitter. The first optical detector 608 is configured to detect incident light 1006 that returns to the first optical detector 608 from either the first optical emitter 606, the second optical emitter 906, or both. It will be appreciated that the oxygenation monitoring devices herein can include any combination of one or more optical emitters, optical detectors, and secondary sensors, as described below.

Figure 11:
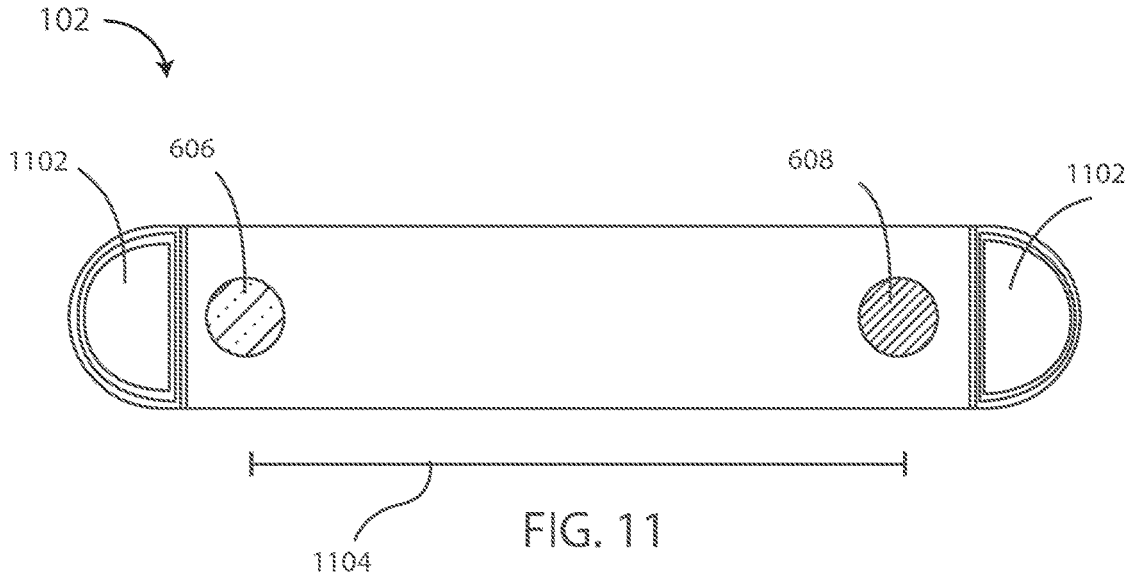
FIG. 11 is a schematic top view of an embodiment of an oxygenation monitoring device in accordance with various embodiments herein.
Figure 12:
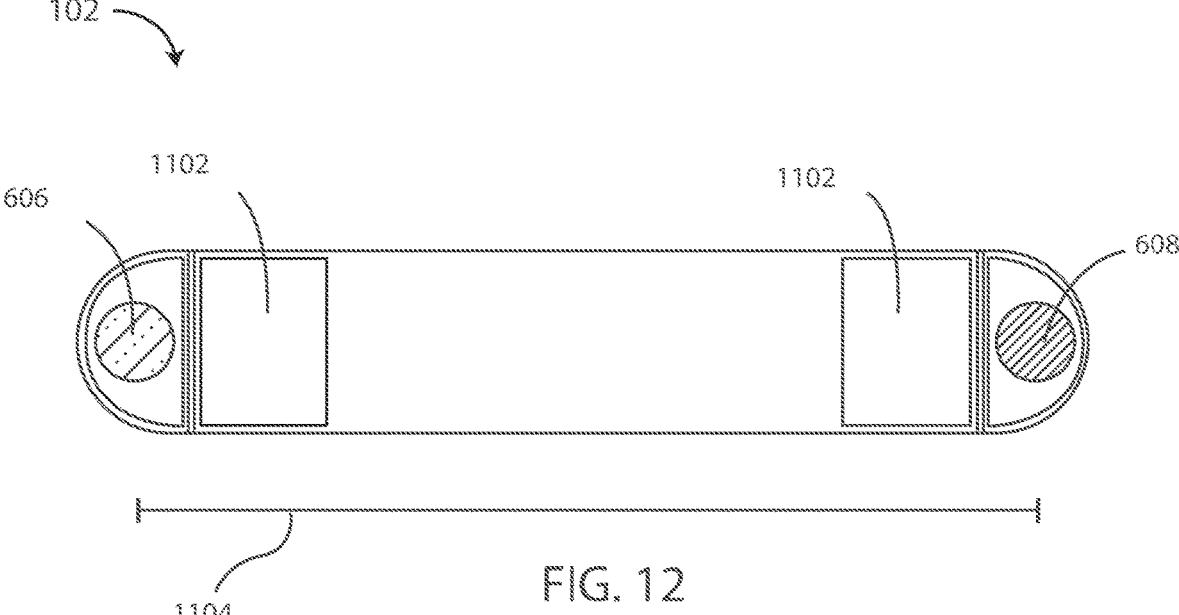
FIG. 12 is a schematic top view of an embodiment of an oxygenation monitoring device in accordance with various embodiments herein.

Referring now to FIGS. 11-12, schematic views of additional embodiments of the oxygenation monitoring devices are shown in accordance with various embodiments herein. The oxygenation monitoring devices 102 can include a first optical emitter 606 and a first optical detector 608. While only one optical emitter and one optical detector are shown in the oxygenation monitoring devices 102 of FIGS. 11-12, it will be appreciated that the oxygenation monitoring devices 102 can include more than one optical emitter, more than one optical detector, and a combination of optical emitters and optical detectors. The oxygenation monitoring devices 102 can further include one or more electrodes 1102 disposed along a length of the oxygenation monitoring devices 102. Electrodes 1102 can be configured to function as part of a secondary sensor (such as an ECG sensor) or, in some embodiments, deliver an electrical stimulation therapy to a patient at or near a treatment site, as will be discussed elsewhere herein.

The first optical emitter 606 and the first optical detector 608, as shown in FIGS. 11 and 12 can be disposed along a length of the oxygenation monitoring device separated by a predetermined distance 1104. Predetermined distance 1104 can include a distance such that the first optical emitter 606 and the first optical detector 608 are spaced along a length of the oxygenation monitoring device from 1 cm to 10 cm apart. In some embodiments, a predetermined distance 1104 between the first optical emitter and the first optical detector can be greater than or equal to 1 cm, 2 cm, 3 cm, 4 cm, 5 cm, 6 cm, 7 cm, 8 cm, 9 cm, 10 cm, 11 cm, 12 cm, 13 cm, 14 cm, or 15 cm, or can be an amount falling within a range between any of the foregoing.

In FIG. 11, the first optical emitter 606 and the first optical detector 608 are positioned between electrodes 1102. In some cases, this can be advantageous because depending on the overall dimensions of the device there may be limited space inside of the device in the areas at the ends of the device. However, in FIG. 12, the first optical emitter 606 and the first optical detector 608 are positioned outside of electrodes 1102. In some cases, this can be advantageous to achieve a maximal spacing between the emitter and detector for a given overall device size. This can be important because a significant factor in the depth of light propagation through the tissue is the distance between the emitter and the detector where a greater distance generally results in a greater depth of propagation through the tissue.

Figure 13:
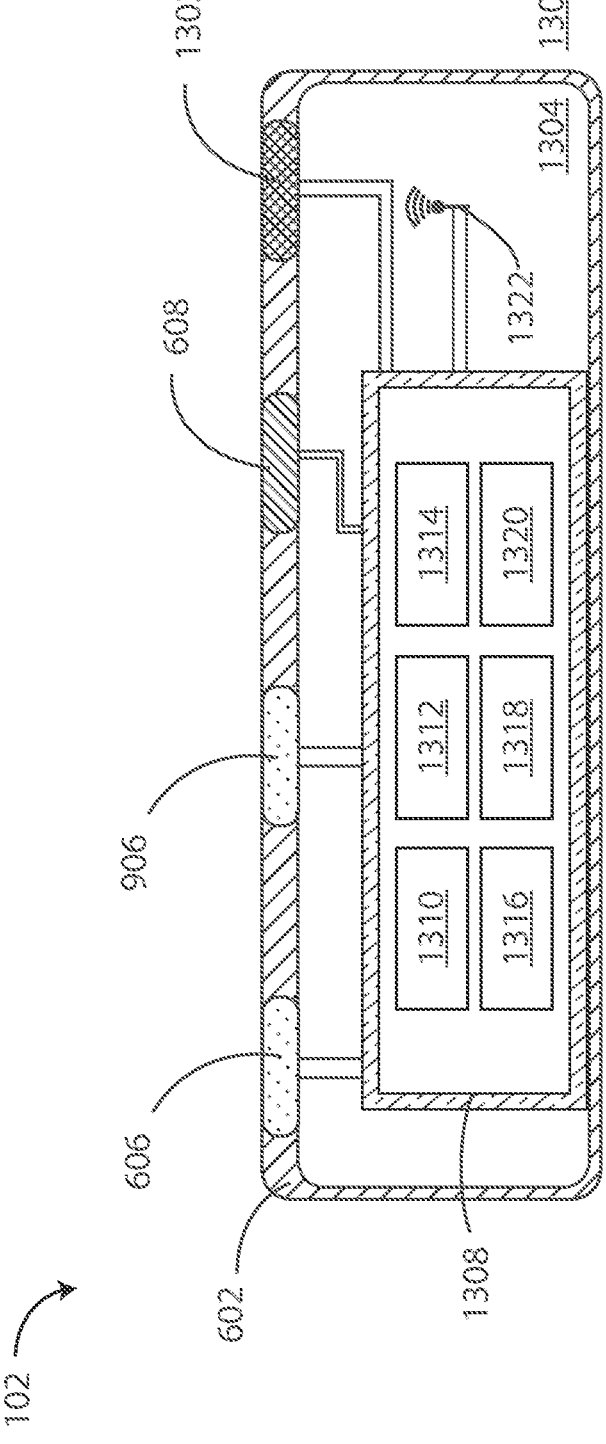
FIG. 13 is a schematic cross-sectional view of an implantable medical device in accordance with various embodiments herein.

Referring now to FIG. 13, a schematic cross-sectional view of an oxygenation monitoring device 102 is shown in accordance with various embodiments herein. The oxygenation monitoring device 102 can include housing 602. The housing 602 of oxygenation monitoring device 102 can include various materials such as metals, polymers, ceramics, and the like. In some embodiments, all or part of housing 602 can be transparent. In some embodiments, the housing 602 can be a single integrated unit. In other embodiments, the housing 602 can include housing 602 and header 604, as discussed above. In some embodiments, the housing 602, or one or more portions thereof, can be formed of a biocompatible metal, such as titanium. In some embodiments, one or more segments of the housing 602 can be hermetically sealed.

Housing 602 can define an interior volume 1304 that in some embodiments is hermetically sealed off from the area 1306 outside of oxygenation monitoring device 102. The oxygenation monitoring device 102 can include control circuitry 1308. Control circuitry 1308 can include various components, such as components 1310, 1312, 1314, 1316, 1318, and 1320. In some embodiments, some or all of these components can be integrated and in other embodiments these components can be separate. In some embodiments, the components can include one or more of a microprocessor, memory circuitry (such as random-access memory (RAM) and/or read only memory (ROM)), recorder circuitry, telemetry circuitry, measurement circuitry, chemical sensor interface circuitry, power supply circuitry (which can include one or more batteries), normalization circuitry, oxygenation monitoring device control circuitry, optical emitter control circuitry, optical detector control circuitry, and the like. In some embodiments, recorder circuitry can record the data produced by the oxygenation monitoring device and record time stamps regarding the same. In some embodiments, the circuitry can be hardwired to execute various functions, while in other embodiments the circuitry can be implemented as instructions executing on a microprocessor or other computation device. In various embodiments, oxygenation monitoring device further includes a measurement circuit configured to control operation of the first optical emitter and the first optical detector A telemetry interface 1322 can be provided for communicating with external devices such as a programmer, a home-based unit, and/or a mobile unit (e.g., a cellular phone, portable computer, etc.) or a wearable medical device. In some embodiments telemetry interface 1322 can be provided for communicating with implanted devices such as a therapy delivery device (e.g., a pacemaker, cardioverter-defibrillator, or the like) or monitoring-only device (e.g., an implantable loop recorder). In some embodiments, the circuitry can be implemented remotely, via either near-field, far-field, conducted, intra-body or extracorporeal communication, from instructions executing on any of the external or the implanted devices, etc. In some embodiments, the telemetry interface 1322 can be located within housing 602. In some embodiments, the telemetry interface 1322 can be located in header 604.

Various optical emitters, optical detectors, and other secondary sensors as described elsewhere herein can be in electrical communication with the circuitry. FIG. 13, shows a first optical emitter 606, a second optical emitter 906, a first optical detector 608 and a secondary sensor 1302 in electrical communication with the control circuitry 1308 within the interior volume 1304. In some embodiments, the control circuitry 1308 is configured to selectively activate first optical emitter 606, the second optical emitter 906, the first optical detector 608 and the secondary sensor 1302. It will be appreciated that the control circuitry 1308 can be configured to selectively activate any number of optical emitters, optical detectors, and secondary sensors.

The secondary sensor 1302 can include, but is not limited to, one or more of a pulse oximetry sensor, a chemical sensor, a posture sensor, or a heart rate sensor. The secondary sensor 1302 can be configured to use electrical, optical, pressure, acoustic, or other techniques. In one example, the secondary sensor 1302 can include one or more electrodes in order to detect electrical properties including, but not limited, to impedance, electrical potential such as in the case of an ECG signal, and the like. In another example, the secondary sensor 1302 can include a microphone or device to detect pressure waves or vibration such as an accelerometer to detect characteristics sounds associated with the heart, lungs, or other physiological activity. In another example, the secondary sensor 1302 can include an accelerometer to detect posture. Aspects of exemplary chemical sensors are described in U.S. Pat. Nos. 7,809,441 and 8,126,554, the content of which is herein incorporated by reference.

It will be appreciated that there can be advantages associated with spacing emitters and detectors as far apart as possible to achieve deep tissue propagation of the emitted light. Generally, a limit on maximum spacing is the overall dimensions of the device and/or portions thereof such as the housing. However, in some embodiments, to achieve greater spacing, another structure can be attached to the device and components such as the emitter and/or detector can be mounted thereon. In this way, a maximum distance of separation can be increased based on the length of the structure added. Such a structure can take various forms. In some embodiments, the structure can be substantially rigid while in other embodiments the structure can be flexible. While not intending to be bound by theory it can be advantageous to include a flexible structure because a long rigid device can be more likely to cause discomfort for the individual into which the device is implanted (in an implantable embodiment). Thus, in various embodiments, the oxygenation monitoring device can include a flexible member. Flexible members embodied herein can assume many shapes, sizes, and configurations suitable for placement within a patient. In some embodiments, the flexible member can be substantially hollow other than components disposed therein. In some embodiments, the flexible member can be non-hollow and filled with a material such as a polymer, a composite, or the like. In contrast, the housing 602 can be substantially rigid. However, in other embodiments the housing 602 itself can also be flexible.

Figure 14:
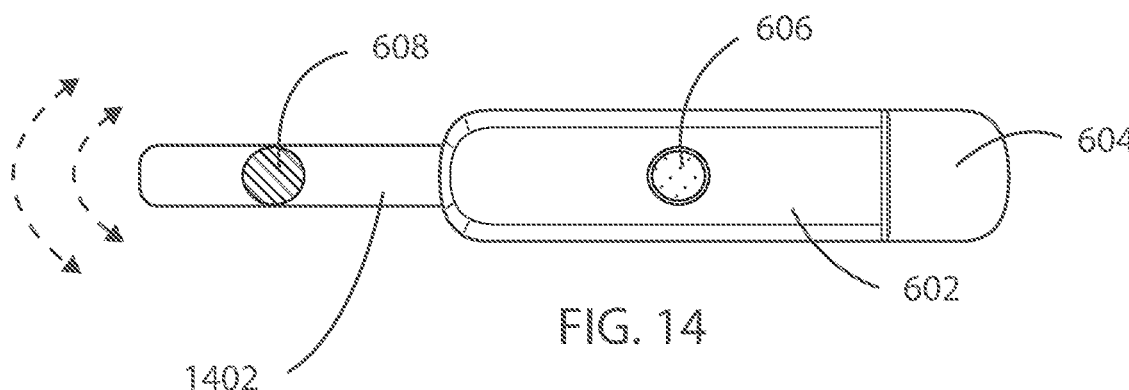
FIG. 14 is a schematic top view of an embodiment of an oxygenation monitoring device in accordance with various embodiments herein.
Figure 15:
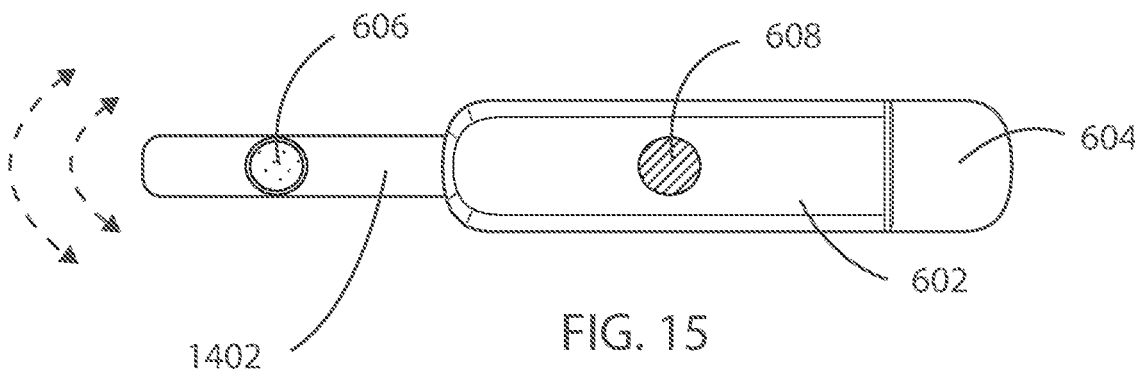
FIG. 15 is a schematic top view of an embodiment of an oxygenation monitoring device in accordance with various embodiments herein.
Figure 16:
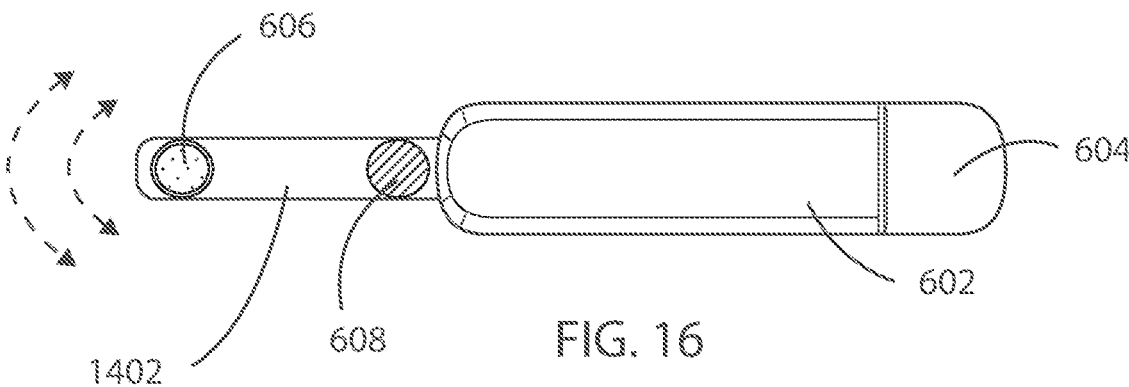
FIG. 16 is a schematic top view of an embodiment of an oxygenation monitoring device in accordance with various embodiments herein.

Referring now to FIGS. 14-16 schematic top plan views of an oxygenation monitoring device having a flexible member are shown in accordance with various embodiments herein. Specifically referring to FIG. 14, the oxygenation monitoring device 102 is shown including a housing 602 and a header 604 coupled to the housing 602. The oxygenation monitoring device 102 can further include a flexible member 1402 extending form the housing 602. In various embodiments, the flexible member 1402 can be connected to the housing and extend outward in a direction away from housing 602. As depicted in FIG. 14, the flexible member 1402 can extend outwards from the housing 602 on the opposite side of the housing from the header 604. Alternatively, the flexible member 1402 can extend outwards from the housing 602 on the same side of the housing from the header 604 and/or be an appendage of the header 604 itself. The flexible member 1402 can be constructed from various materials including, for example, a material configured to be bent without damage. In some embodiments, the flexible member 1402 can be formed of a material such as a polymer, an elastomeric polymer, a flexible composite, or the like. In some embodiments, the flexible member 1402 can be of substantially the same diameter and/or circumference as the housing 602, but in other embodiments can be greater or lesser (such as depicted in FIGS. 14-16) in diameter and/or circumference. While not shown in FIGS. 14-16, one or more conductors can interconnect the flexible member and components disposed thereon such as an emitter and/or detector with the other components of the device that may be housed in housing 602.

It will be appreciated that various combination of optical emitters and optical detectors can be used when a flexible member is present in the oxygenation monitoring devices herein. In various embodiments, the first optical emitter is disposed along a length of the flexible member, while the first optical detector is disposed along the housing. In various embodiments, the first optical detector is disposed along a length of the flexible member, while the first optical emitter is disposed along the housing. In other embodiments, the first optical emitter and the first optical detector are both disposed along a length of the flexible member. However, it is to be understood that various combinations of one or more optical detectors, one or more optical emitters, one or more secondary sensors can be disposed along an oxygenation monitoring device having a flexible member. It will be further understood that in various embodiments, the optical emitters and optical detectors can be disposed together on the same side of the oxygenation monitoring device, while the secondary sensors can be disposed on the opposite side of the oxygenation monitoring device.

The flexible member can take on various dimensions in the length, width, and thickness directions. In a particular embodiment herein, the flexible member can be approximately 1 to 5 cm in length, 0.25 cm to 1.5 cm wide, and 0.25 cm to 1.0 cm thick. In various embodiments, the flexible member is from 1 centimeters (cm) to 3 cm in length. In some embodiments, the length of flexible member 1402 can be greater than or equal to 1 cm, 2 cm, 3 cm, 4 cm, or 5 cm, or more or can be an amount falling within a range between any of the foregoing. In some embodiments, the flexible member 1402 can be about 0.25 cm, 0.5 cm, 0.75 cm, 1.0 cm, or 2.0 cm in width. In some embodiments the length can be in a range wherein any of the foregoing widths can serve as the upper or lower bound of the range, provided that the upper bound is greater than the lower bound. In some embodiments, the flexible member 1402 can be about 0.25 cm, 0.50 cm, 0.75 cm or 1.0 cm, 1.25 cm, 1.50 cm, 1.75 cm, or 2.0 cm thick, or can be an amount falling within a range between any of the foregoing. In some embodiments the thickness can be in a range wherein any of the foregoing thicknesses can serve as the upper or lower bound of the range, provided that the upper bound is greater than the lower bound.

In the embodiment of FIG. 14, the oxygenation monitoring device 102 can include a first optical emitter 606 coupled to the housing and a first optical detector 608 coupled to the flexible member 1402. However, it will be appreciated that the first optical emitter 606 and the first optical detector 608 can be positioned at any location along the oxygenation monitoring device 102, including the flexible member 1402 to achieve optimal propagation of light through the tissue of a patient.

Referring now to FIG. 15, an oxygenation monitoring device 102 is shown in accordance with the embodiments herein. The oxygenation monitoring device 102 can include a housing 602, a header 604 coupled to the housing 602, and a flexible member 1402 extending from the housing 602. In the embodiment of FIG. 15, the oxygenation monitoring device 102 can include a first optical emitter 606 coupled to the flexible member 1402 and a first optical detector 608, coupled to the housing 602.

In some cases, both an emitter and a detector can be disposed on the flexible member. Referring now to FIG. 16, an oxygenation monitoring device 102 is shown in accordance with the embodiments herein. The oxygenation monitoring device 102 can include a housing 602, a header 604 coupled to the housing 602, and a flexible member 1402 extending from the housing 602. The oxygenation monitoring device 102 can include a first optical emitter 606 and a first optical detector 608 each coupled to the flexible member 1402.

While only one optical emitter and one optical detector are shown in the oxygenation monitoring devices 102 of FIGS. 14-16, it will be appreciated that the oxygenation monitoring devices 102 can include more than one optical emitter, more than one optical detector, and a combination of optical emitters and optical detectors disposed anywhere across the length of the oxygenation monitoring device.

Figure 17:
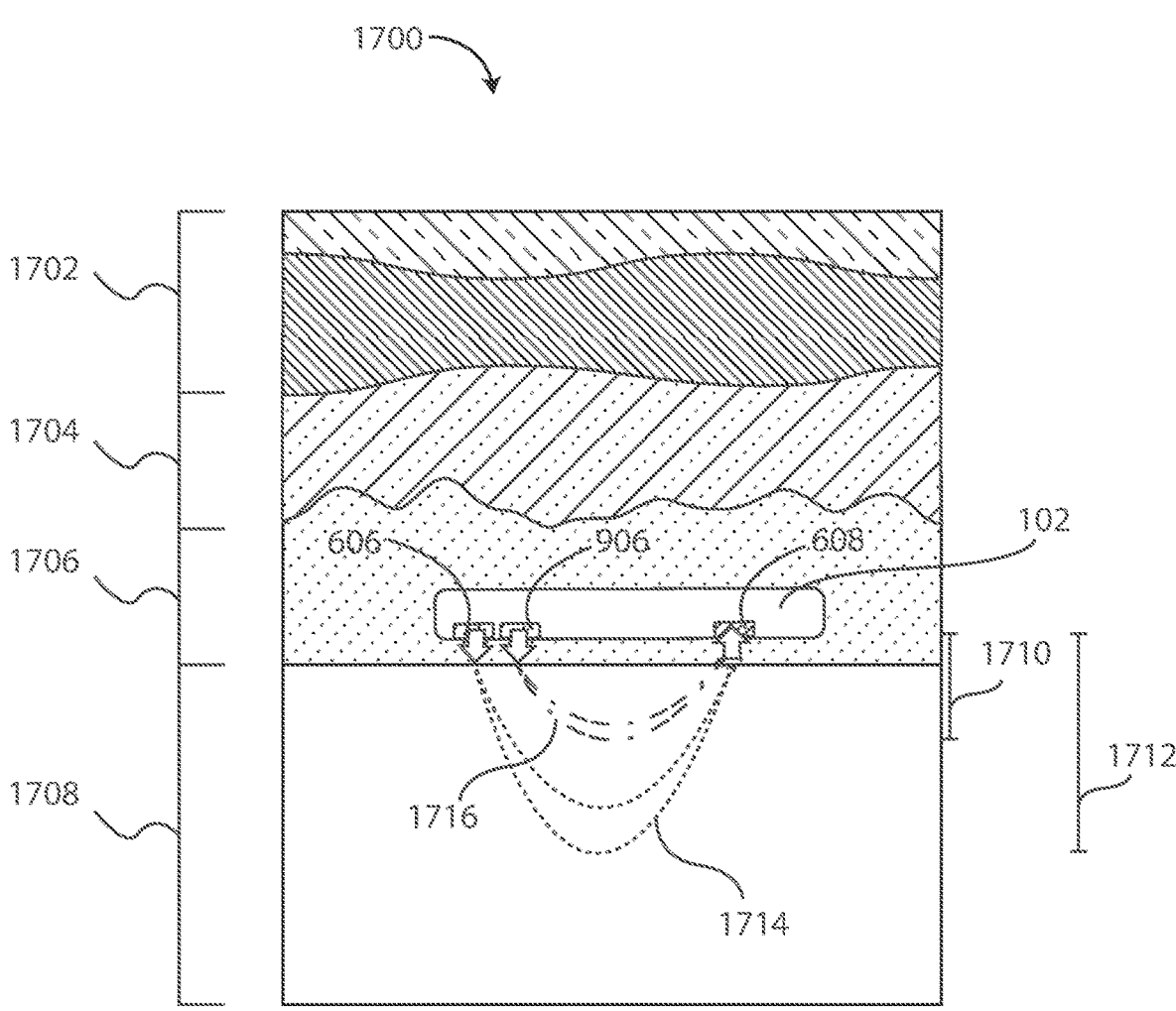
FIG. 17 is a schematic cross-sectional view of an implanted oxygenation monitoring device in accordance with various embodiments herein.

The oxygenation monitoring devices herein can be implanted within various subcutaneous implantation sites or other regions of the inside of the body. Referring now to FIG. 17, a schematic cross-sectional view of a subcutaneous implantation site 1700 with an implanted oxygenation monitoring device 102 is shown in accordance with various embodiments herein. Human skin includes multiple layers including the epidermis 1702 and the dermis 1704. Beneath the layers of human skin and typically above a layer of muscle 1708 is the subcutaneous space that can include a layer of adipose tissue 1706. It will be appreciated that the subcutaneous space further includes additional anatomical structures such as blood vessels, fascia, lymphatic vessels, nervous tissue, hair follicles, and the like.

The oxygenation monitoring device 102 can be disposed at any location within the subcutaneous space. In various embodiments, the oxygenation monitoring device 102 can even be implanted deeper within the body, such as within underlying muscle, within a cavity, such as the chest cavity, adjacent to or within an internal organ of the body, within a blood vessel, or the like. In various embodiments, the oxygenation monitoring device 102 can be held in place via sutures. In some embodiments, the oxygenation monitoring device 102 can include one or more apertures to facilitate its fixation via sutures. The oxygenation monitoring device 102 can be implanted within a patient such that each of the optical emitters and optical detectors included on the oxygenation monitoring device 102 are disposed facing the interior of a patient's body and are directed toward the volume of the tissue to be monitored. In some embodiments, the tissue to be monitored includes lung tissue, airway tissue, cardiovascular tissue, and the like. Implanting the oxygenation monitoring device 102 facing the interior of a patient's body can selectively direct emitted light toward tissues to be illuminated inside the patient's body.

The oxygenation monitoring device 102 shown in FIG. 17 includes a first optical emitter 606, a second optical emitter 906, and a first optical detector 608. In various embodiments, the oxygenation monitoring device 102 can be configured such that the emitted light 1714 from the first optical emitter 606 at a first wavelength is propagated to a first depth 1710 from a surface of the oxygenation monitoring device 102, and the emitted light 1716 from the second optical emitter 906 at a second wavelength is propagated to a second depth 1712 from a surface of the oxygenation monitoring device 102. In various embodiments, the oxygenation monitoring device 102 can be configured such that emitted light 1714 from the first optical emitter 606 is propagated to a different depth than emitted light 1716 from the second optical emitter 906.

In various embodiments, the depth of emitted light propagated into the tissue of the patient can be tailored by changing the distance between the first optical emitter 606 and second optical emitter 906, and the first optical detector 608, where various distances suitable for use between the optical emitters and optical detectors are discussed elsewhere herein. In some embodiments, the depth of emitted light propagated into the tissue of the patient can also be tailored by selecting various wavelengths of light to be emitted by the first optical emitter 606 and second optical emitter 906. In some embodiments, the first wavelength and second wavelength are different wavelengths. Wavelengths suitable for use in the oxygenation monitoring devices described are discussed elsewhere herein.

Without being bound by any particular theory, it is believed that light generally follows a direct path through a medium in the absence of scattering factors. However, in more complex media where scattering is prevalent, it is believed that light propagation through such media occurs by way of random scattering. Biological tissue is complex, as it is comprised of many tissue types with complex molecules and compounds distributed therein. It is believed that light propagation through biological tissue is due to scattering as caused by the difference in the index of refraction of the various molecules and compounds in the tissues. By way of example, scattering of light can occur in the blood due to the difference of the index of refraction between red blood cells and plasma, and can occur in other tissues due to the difference of the index of refraction between cells, including cellular organelles, and cellular fluids, such as intracellular fluids and extracellular fluids. The resultant path for the emitted light from the optical emitter to the optical detector through biological tissues can assume a broad, arc-shaped optical path as it returns to the optical detector. The arc-shaped optical path becomes deeper as the distance between the emitter and detector increases (all other factors being equal).

Figure 18:
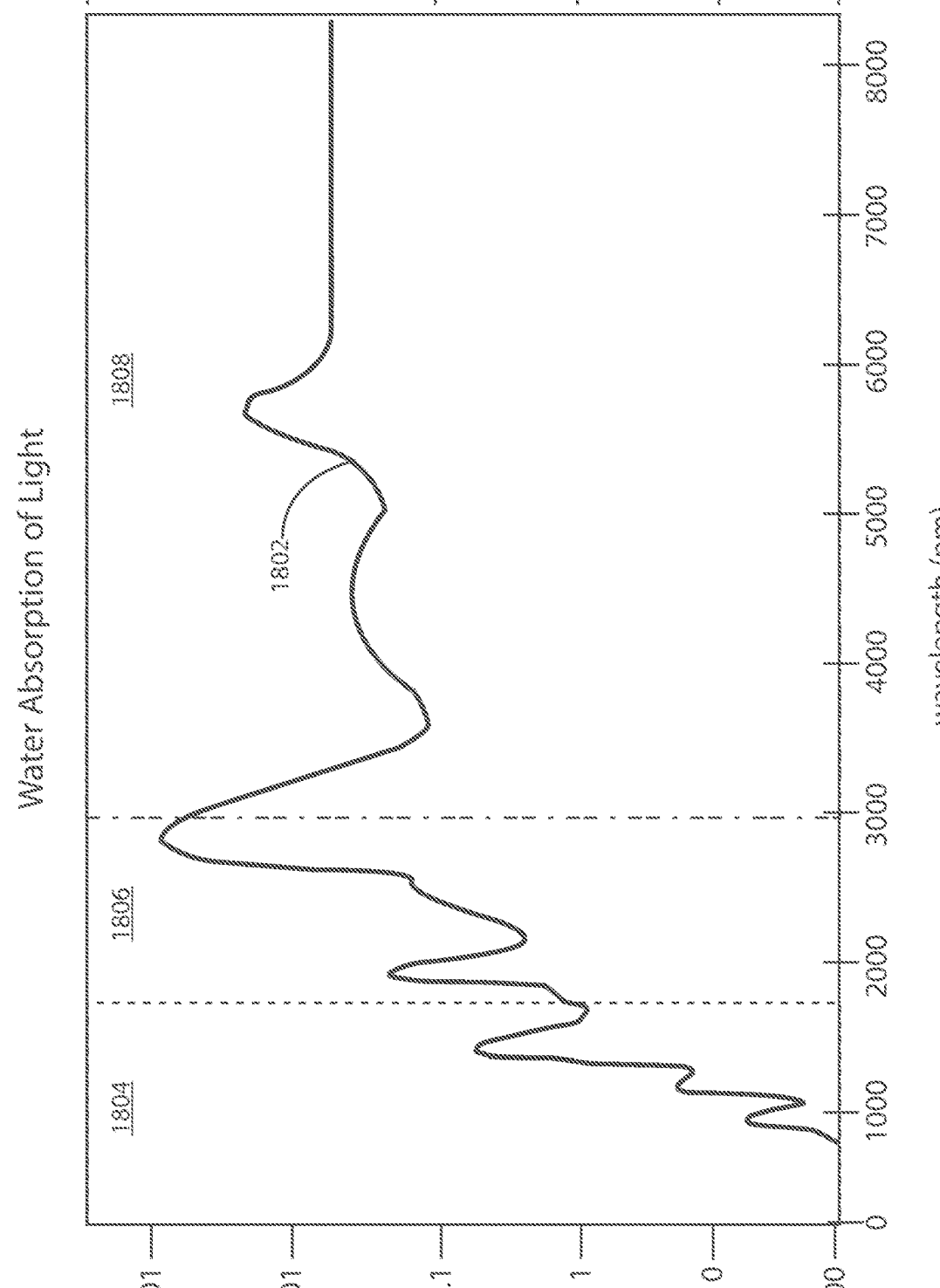
FIG. 18 is a representative plot of tissue penetration depth of light at various tissue depths in accordance with various embodiments herein.

Referring now to FIG. 18, a graphical representation of water absorption of light in various tissues is shown in accordance with the embodiments herein. The tissue penetration depth in millimeters (mm) as a function of wavelength in nanometers (nm) is represented as plot 1802. At wavelengths of from 700 nm to 1500 nm, represented in section 1804 of plot 1802, the tissue penetration depth is from roughly 5 mm to 100 mm, which includes depths that penetrate within the epidermis, muscle, internal organs. At wavelengths of from 1500 nm to 3000 nm, represented in section 1806 of plot 1802, the tissue penetration depth is only from roughly 1 mm to 0.001 mm, which includes portions of the epidermis and the skin surface. At wavelengths greater than 3000 nm, represented in section 1808 of plot 1802, the tissue penetration depth is only 0.1 mm or less, which includes superficial portions of the epidermis and the skin surface. Thus, as can be seen, the specific wavelength chosen impacts the maximum depth of propagation through the tissue. In embodiments herein, wavelengths are selected (as also described elsewhere herein) to provide for deep tissue propagation of the emitted light.

Figure 19:
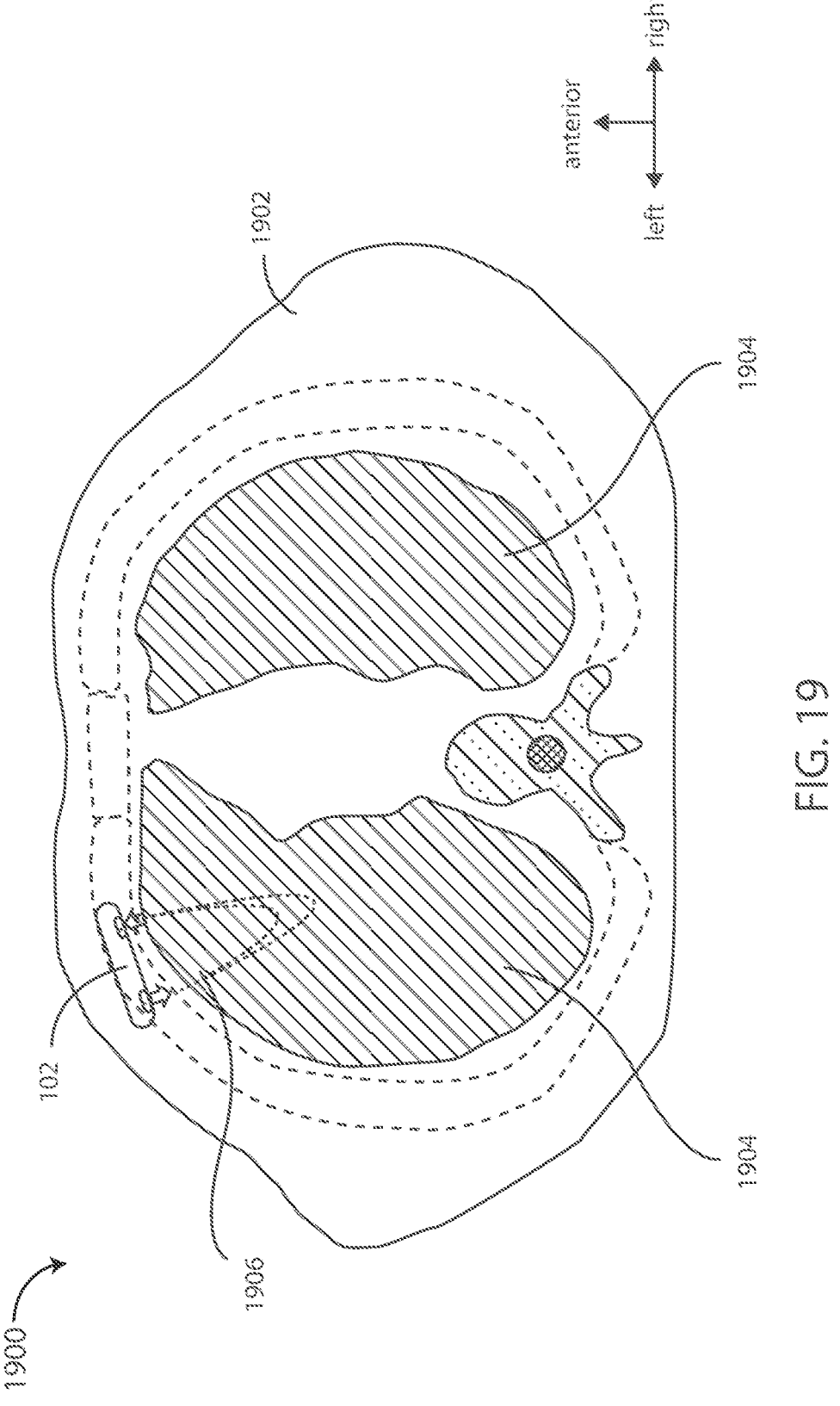
FIG. 19 is a schematic cross-sectional view of an implanted oxygenation monitoring device in accordance with various embodiments herein.

Referring now to FIG. 19, a schematic diagram of a cross-sectional view 1900 of a human thorax 1902 is shown in accordance with the embodiments herein. The cross-sectional view 1900 of the human thorax 1902 includes the left and right lungs 1904. An oxygenation monitoring device 102 is shown positioned within an intercostal space with an optical emitter and an optical detector disposed facing a surface of the lung tissue. The oxygenation monitoring device 102 is shown disposed facing the interior of a patient's body and is directed toward the surface of the tissue to be monitored. In some embodiments, the tissue to be monitored includes lung tissue, cardiovascular tissue, and the like. Implanting the oxygenation monitoring device 102 facing the interior of a patient's body can selectively direct emitted light 1906 toward tissues to be illuminated inside the patient's body.

Figure 20:
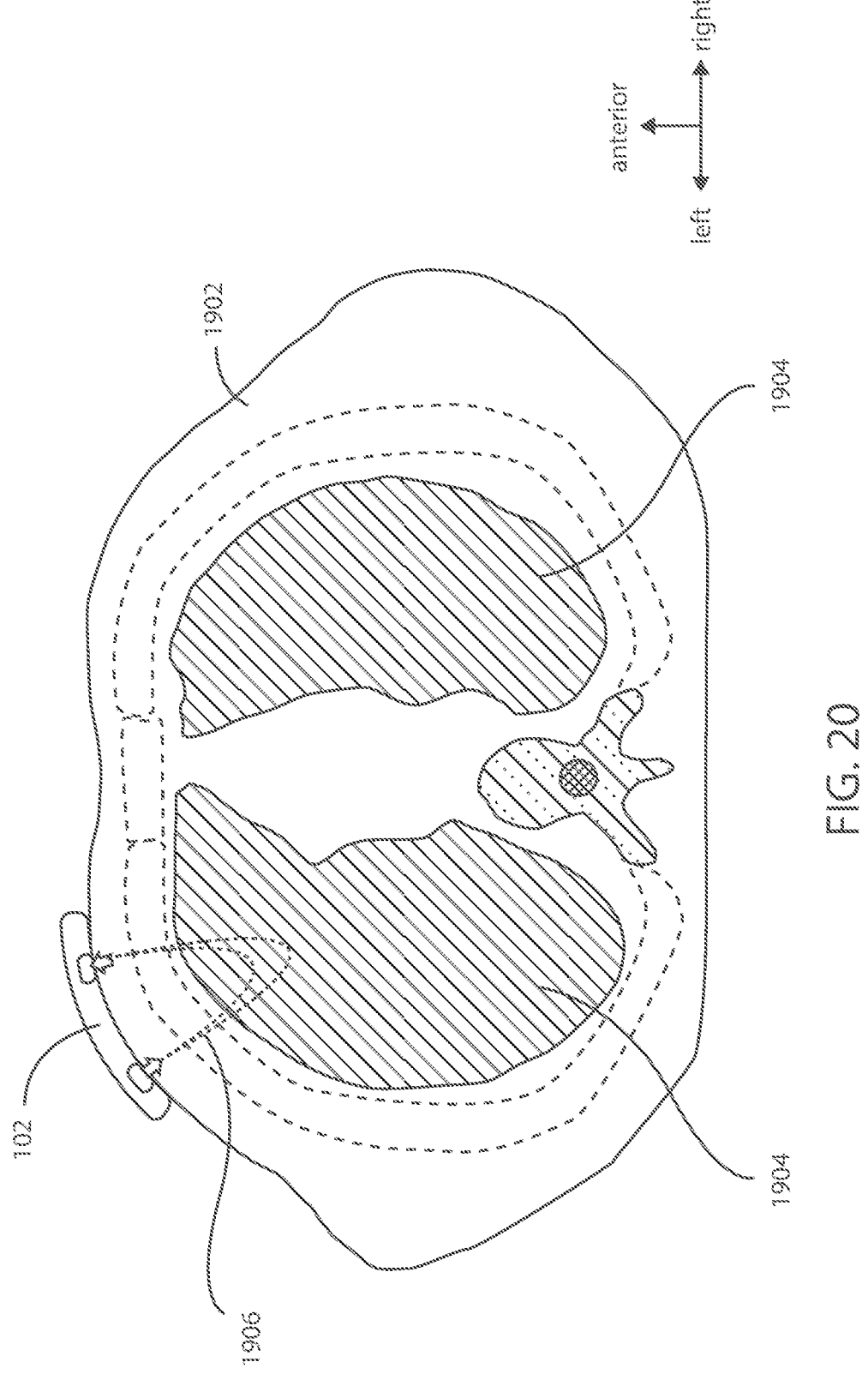
FIG. 20 is a schematic cross-sectional view of a wearable oxygenation monitoring device in accordance with various embodiments herein.

Referring now to FIG. 20, a schematic diagram of a cross-sectional view 1900 of a human thorax 1902 is shown in accordance with the embodiments herein. The cross-sectional view 1900 of the human thorax 1902 includes the left and right lungs 1904. An oxygenation monitoring device 102 having an optical emitter and optical detector is shown externally positioned on the skin and over an intercostal space. The oxygenation monitoring device 102 can be held in place using a wearable strap, such as described with respect to FIG. 3, or using an adhesive, or other skin mountable fixation device. The oxygenation monitoring device 102 is shown disposed facing the interior of a patient's body and is directed toward the surface of the tissue to be monitored. In some embodiments, the tissue to be monitored can include lung tissue, airway tissue, cardiovascular tissue, or any other anatomical structure of interest in the body the like. Implanting the oxygenation monitoring device 102 with the emitter(s) and detector(s) thereof facing the interior of a patient's body can selectively direct emitted light 1906 toward tissues to be illuminated inside the patient's body.

Figure 21:
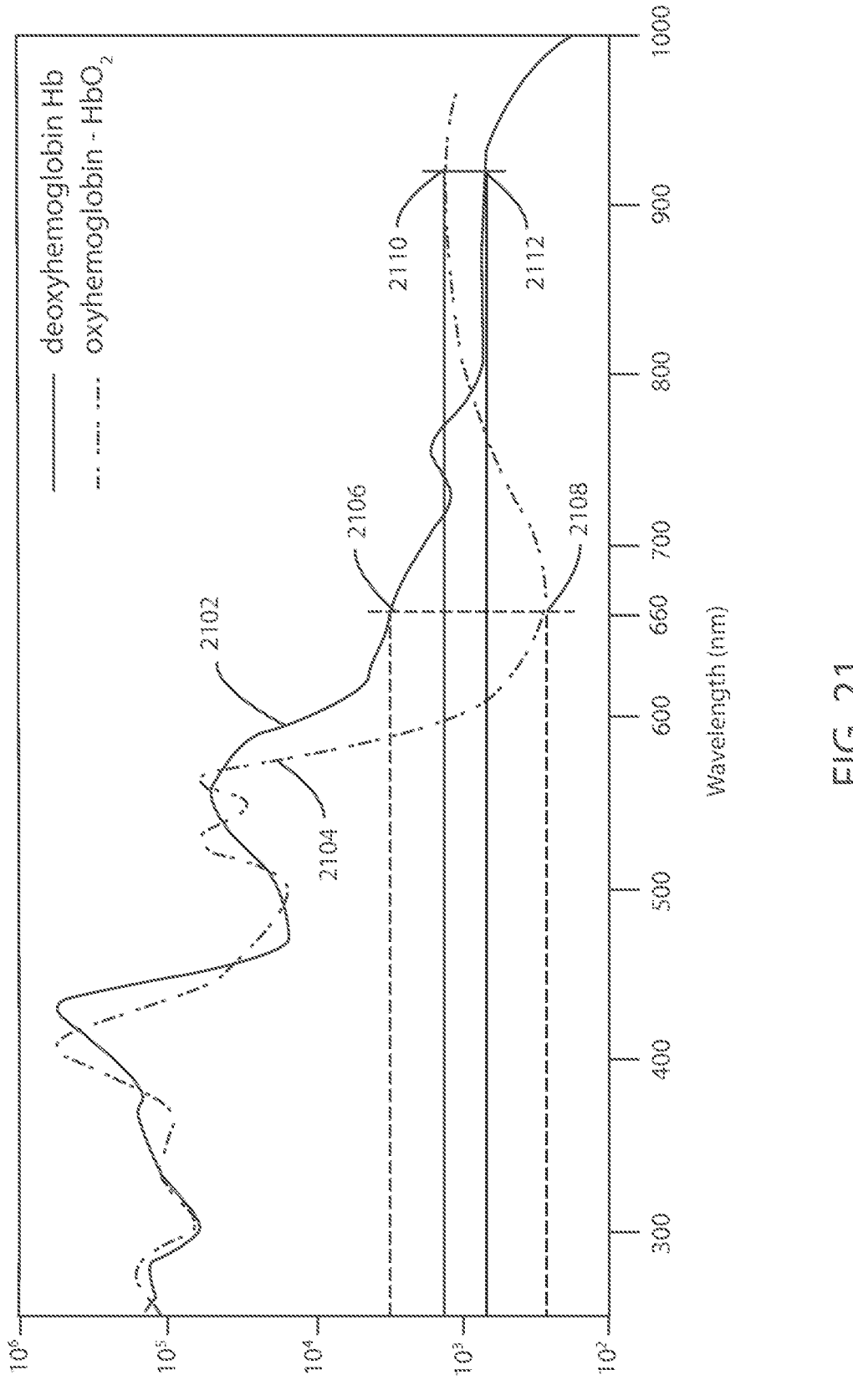
FIG. 21 is a representative plot of molar extinction coefficient versus wavelength for hemoglobin in accordance with various embodiments herein.

Referring now to FIG. 21, a representative plot of the molar extinction coefficient ($cm^{-1}$, $mol^{-1}$, L) versus wavelength showing hemoglobin absorption of light in various tissues in accordance with the embodiments herein. Plot 2102 represents the absorption of light by deoxygenated hemoglobin (i.e., deoxyhemoglobin—Hb) at various wavelengths as a function of molar extinction coefficient ($cm^{-1}$, $ml^{-1}$, L). Plot 2104 represents the absorption of light by oxygenated hemoglobin (i.e., oxyhemoglobin—$HbO_2$) at various wavelengths as a function of molar extinction coefficient ($cm^{-1}$, $ml^{-1}$, L). In various embodiments herein, when determining tissue oxygenation, a ratio of the molar extinction coefficient ($cm^{-1}$, $ml^{-1}$, L) at two wavelengths can be used to refine the measurement, where the first wavelength is chosen where the molar extinction coefficient ($cm^{-1}$, $ml^{-1}$, L) of deoxyhemoglobin is greater than the molar extinction coefficient ($cm^{-1}$, $ml^{-1}$, L) of oxyhemoglobin, and the second wavelength is chosen where the molar extinction coefficient ($cm^{-1}$, $ml^{-1}$, L) of deoxyhemoglobin is less than the molar extinction coefficient ($cm^{-1}$, $ml^{-1}$, L) of oxyhemoglobin. By way of example, a measurement at a first wavelength can be recorded at 660 nm, where the molar extinction coefficient ($cm^{-1}$, $ml^{-1}$, L) of deoxyhemoglobin is greater than that of oxyhemoglobin, and a measurement at a second wavelength can be recorded at 900 nm where the molar extinction coefficient ($cm^{-1}$, $ml^{-1}$, L) of deoxyhemoglobin is less than that of oxyhemoglobin.

As shown in FIG. 21, the molar extinction coefficient 2106 of deoxyhemoglobin at 660 nm is greater than the molar extinction coefficient 2108 of oxyhemoglobin at 660 nm. The molar extinction coefficient 2112 of deoxyhemoglobin at 900 nm is less than the molar extinction coefficient 2110 of oxyhemoglobin at 660 nm. While the example shown in FIG. 21 utilizes the first and second wavelengths at 660 nm and 900 nm, respectively, it will be appreciated that the first wavelength can be chosen anywhere the molar extinction coefficient of deoxyhemoglobin is greater than the molar extinction coefficient of oxyhemoglobin; and the second wavelength can be chosen where the molar extinction coefficient of deoxyhemoglobin is less than the molar extinction coefficient of oxyhemoglobin. As shown in the figure there are many potential combinations that will work. Some of these are outside the 650 to 900 nm range. As discussed elsewhere herein, the first wavelength can be selected from 100 nanometers (nm) to 2000 nm, or any range as disclosed herein, and the second wavelength can be selected from 800 nm to 2000 nm, or any range as disclosed herein.

Pulmonary Ventilation and Perfusion

Figures 22, 23:
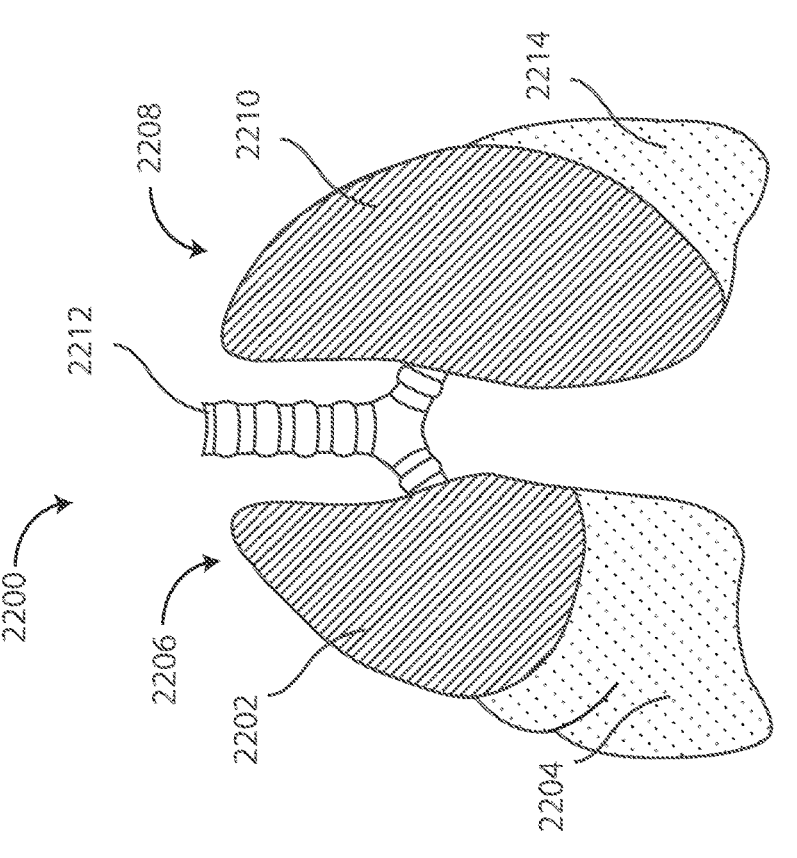
FIG. 22 is a schematic representation of human lungs in accordance with various embodiments herein.
FIG. 23 is a diagram of various disease states in accordance with various embodiments herein.

In various embodiments herein, the device and/or system can provide information regarding pulmonary ventilation and/or perfusion status and/or mismatch. Referring now to FIG. 22, a schematic view of human lungs is shown in accordance with various embodiments herein. The human pulmonary system 2200 includes the right lung 2206, the left lung 2208, and the trachea 2212 and associated bronchial tree. Right lung 2206 includes a right upper portion 2202 and a right lower portion 2204. Left lung 2208 includes a left upper portion 2210 and a left lower portion 2214. Oxygenation status of the lung tissue can be indicative of a pulmonary ventilation or perfusion status. Oxygenation status can be used to determine a disease state in a patient. Various disease states are a result of issues that arise with the ventilation and perfusion processes in a patient.

Ventilation (V) is the process of inhalation of air into the lungs. During inhalation, oxygen from the air gets transported into the lungs and is exchanged into the bloodstream at the capillaries surrounding myriad alveoli deep in the lung tissue. Perfusion (Q) is the process of blood flow throughout the vasculature within a tissue. For example, when deoxygenated blood travels from the heart and to the capillaries surrounding the alveoli deep in the lung tissue, carbon dioxide is released and oxygen is absorbed. A ratio of ventilation to perfusion can be defined by an amount of air that reaches the alveoli deep within the lungs to an amount of blood flow to that same tissue. When ventilation and perfusion function normally, the ventilation-perfusion ratio provides adequate blood flow and oxygenation to sustain sufficient oxygenation within a patient to meet the oxygen demands of the body. When the ventilation and perfusion are out of sync, a ventilation-perfusion (V/Q) mismatch occurs and results in a change in lung oxygenation. In some embodiments, the change in lung oxygenation can be a reduced lung oxygenation. Reduced lung oxygenation can occur under various circumstances. In one example, a portion of the lung tissue receives sufficient oxygen during inhalation without sufficient blood flow. In another example, when the lung tissue receives adequate blood flow but insufficient oxygen during inhalation, reduced oxygenation of the blood can occur. In various disease states, low ventilation affects the lower portion of the lungs. In various other disease states, low perfusion affects the upper portion of the lungs. In various embodiments herein, the device or system can identify circumstances of low ventilation in the lower portion of the lungs and/or low perfusion in the upper portion of the lungs.

Referring now to FIG. 23, a table detailing the relationship between disease and ventilation-perfusion mismatch is shown in accordance with the embodiments herein. In cases of reduced ventilation, disease states that affect the lower portion of the lung can include chronic obstructive pulmonary disease (COPD), pulmonary edema with heart failure with normal cardiac output, asthma, pneumonia, and various airway obstructions. In cases of reduced perfusion, disease states that affect the upper portion of the lung can include heart failure with reduced cardiac output, and pulmonary embolism.

Figure 24:
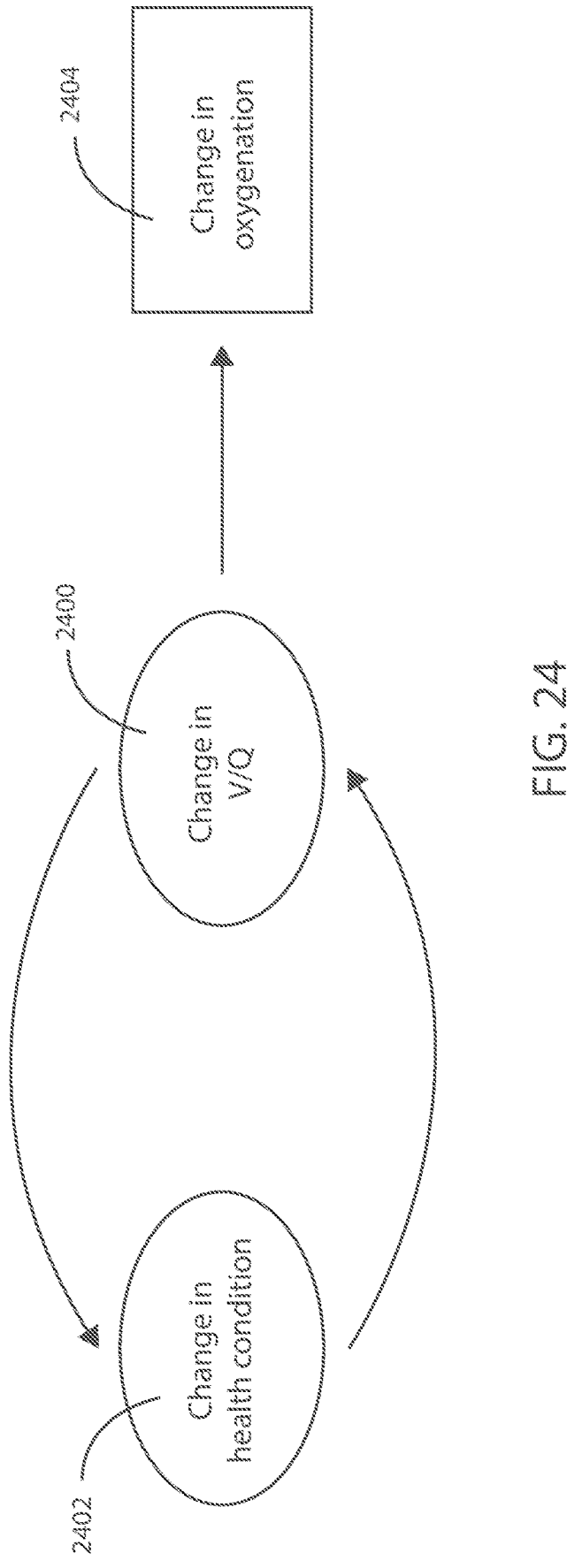
FIG. 24 is a flow diagram of oxygenation status due to a change in ventilation-perfusion in accordance with various embodiments herein.

The disease states described can be monitored with the oxygenation monitoring devices herein by measuring a change in oxygen concentration. Referring now to FIG. 24, a flow diagram of oxygenation status due to a change in ventilation-perfusion is shown in accordance with various embodiments herein. As stated above, a change in either the ventilation (V) or perfusion (Q) status 2400 of a patient can result from or cause a change in health condition 2402 of a patient. Similarly, a change in health condition 2402 of a patient can result from or cause a change in the ventilation or perfusion status 2400 of a patient. Both a change in the ventilation or perfusion status 2400 or a change in a health condition 2402 can result in a change in oxygenation status 2404 in a patient. Thus, it will be appreciated that the oxygenation status of the lung tissue can be indicative of a pulmonary ventilation or perfusion status of a patient. The oxygenation monitoring devices herein can be configured to monitor a progression or regression of one or more conditions comprising chronic obstructive pulmonary disease (COPD), pulmonary edema, asthma, pneumonia, airway obstruction, heart failure, acute respiratory distress syndrome (ARDS), septic shock, or pulmonary embolism. In various embodiments, the change in oxygenation detected by the oxygenation monitoring devices herein can be used to monitor a progression or regression of the one or more conditions described.

The oxygenation status of the lung tissue can be based on the detected incident light alone, or in combination with one or more secondary characteristics obtained from a secondary sensor. In various embodiments, determining the oxygenation status comprises performing a ratiometric calculation using at least one of a measured absorption, light scattering, or phase. In various embodiments, a second optical emitter is configured to emit light at a second wavelength different than the first wavelength (such as described above with regard to FIG. 21) and the ratiometric calculation can be based on detecting incident light from the first optical emitter and second optical emitter.

Tissue Penetration

Spacing of the optical emitters and optical detectors along a length of the oxygenation monitoring devices herein can determine the depth of penetration of the emitted light into the surrounding tissues. By way of non-limiting example, the penetration depth of emitted light can be approximated according to the following equation:

$$\text{light penetration depth} = \sim \frac{1}{2}(\text{spacing between emitter and detector}).$$

In some embodiments, the depth or propagation of the emitter light can be greater than or equal to 1 cm, 2 cm, 3 cm, 4 cm, or 5 cm, or can be an amount falling within a range between any of the foregoing. In various embodiments, the configuration of the oxygenation monitoring device can allow for the propagation of the emitted light into a patient's body and into the lung tissue. In some embodiments, the length between the first optical emitter and the first optical detector can be greater than or equal to 1 cm, 2 cm, 3 cm, 4 cm, 5 cm, 6 cm, 7 cm, 8 cm, 9 cm, 10 cm, 11 cm, 12 cm, 13 cm, 14 cm, or 15 cm, or can be an amount falling within a range between any of the foregoing. In various embodiments, at least 50, 60, 70, 80, 90, 95, 98, or 99 percent of the light incident upon the optical detector and used to determine oxygenation of the tissue has propagated through a tissue at a depth of at least 1 cm, 2 cm, 3 cm, 4 cm, or 5 cm or more as measured from a surface of the device and/or the optical emitter(s) thereof.

Therapies

The devices and systems herein can be configured to deliver a therapy to a patient in response to a change in oxygenation detected by the oxygenation monitoring devices herein. In various embodiments, the oxygenation monitoring devices can be configured to deliver a therapy to a patient. In some embodiments, implantable therapeutic devices can be implanted and used in a system in conjunction with the wearable oxygenation monitoring devices described herein. The implantable therapeutic devices can include, but not be limited to cardiac rhythm management devices, an implantable cardioverter-defibrillator (ICD), a left ventricular assist device (LVAD), a pacemaker, and the like.

In various embodiments, the devices and systems herein can be configured to deliver or modify a pulmonary oxygenation therapy to a patient to treat one or more diseases states or conditions including, but not limited to, chronic obstructive pulmonary disease (COPD), pulmonary edema with heart failure with normal cardiac output or abnormal cardiac output, asthma, pneumonia, various airway obstructions, and pulmonary embolism. In some embodiments, a pulmonary oxygenation therapy can include a command sent to a device such as a ventilation device or other breathing assistance device to change proportions of gases being provided (such as increasing or decreasing oxygen content), change volumes of gases being provided, or the like.

AC/DC Component Calculations

Figure 25:
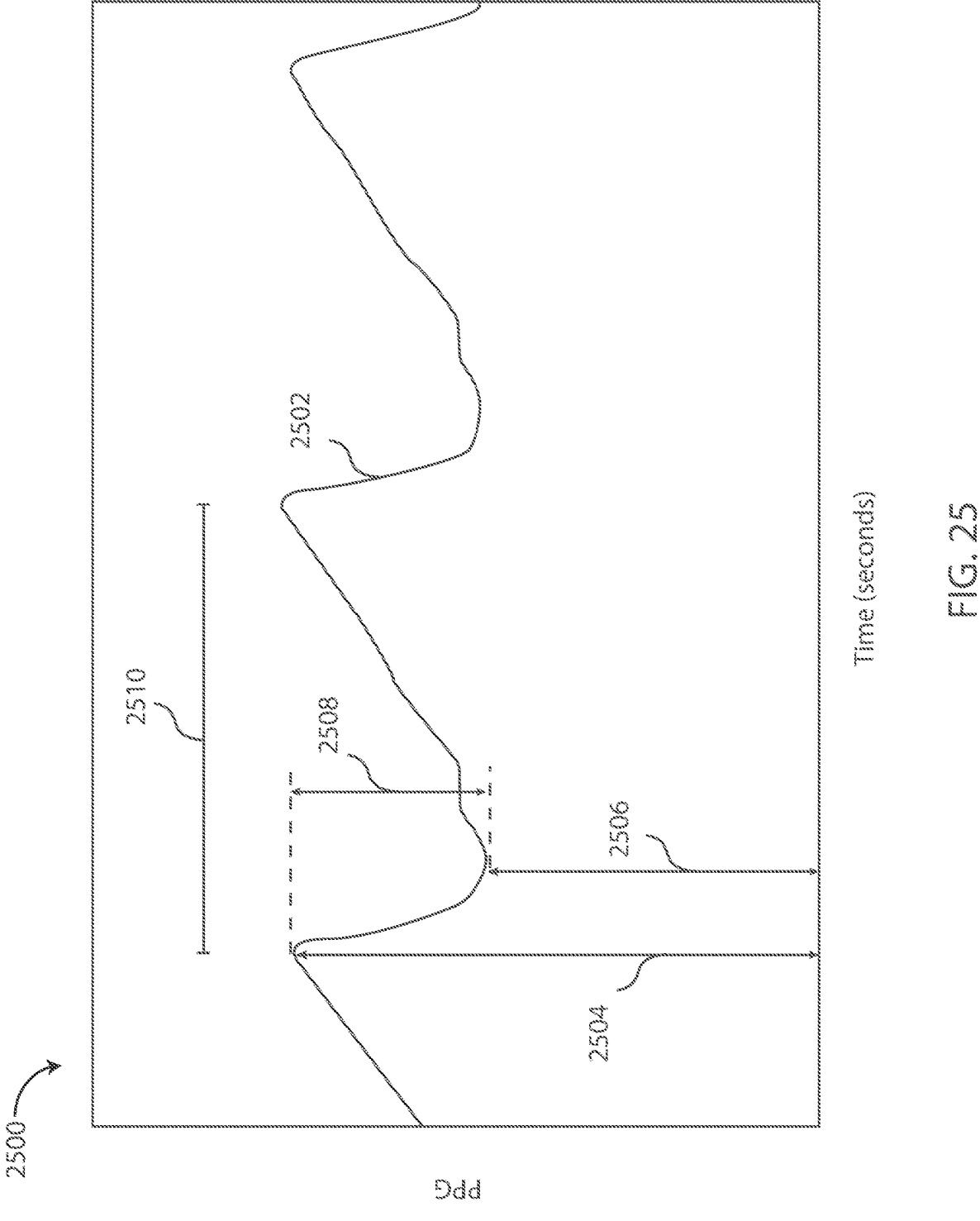
FIG. 25 is a schematic representation oxygenation status versus time in accordance with various embodiments herein.

Referring now to FIG. 25, a graphical representation an optical signal 2500 is shown in accordance with the embodiments herein. The optical signal can be indicative of the incident light measured at the optical detector of an oxygenation monitoring device. As depicted by FIG. 25, the optical signal can be approximately periodic having period 2510, maximum value 2504 at the systolic peak, and minimum value 2506 at the diastolic valley. In this example, the periodicity of the signal is a consequence of the systole and diastole of the cardiac cycle. During systole, the heart contracts, pushing the oxygenated blood towards the periphery of the body, resulting in an increased blood pressure. During diastole, the hear fills with blood, retracting the blood from the periphery of the body resulting in a decrease in blood pressure. Due to the absorption of light by various chromophores in blood, such as oxyhemoglobin and deoxy-hemoglobin, the optical density of the tissue at certain wavelengths can increase during systole and decrease during diastole resulting, in a periodic signal with maximums and minimums. Each cycle of the signal contains a maximum value 2504 at the systolic peak, and minimum value 2506 at the diastolic valley.

The optical signal can, effectively, have an AC (or variable) component 2508 and a DC (or constant) component 2502. The term 'AC', as used herein, refers to a portion of signal that varies relatively rapidly with time. The AC component can be indicative of the portion of the signal originating by pulsations in a patient's blood during each heartbeat. The term 'DC', as used herein signals, refers to portions of the signal that are relatively invariant with time.

As shown and discussed in FIG. 25, the incident light measured by the optical detector of an oxygenation monitoring device can have both an AC and DC components. In various embodiments, both an AC component and a DC component of the light detected by the optical detector are used to determine a property of the tissue (i.e., pulmonary oxygenation status). In various embodiments, the property can be derived from a ratio of the AC and DC components of the signal as measured by the optical detector. In various embodiments, the property can be derived from a ratio of the AC and DC components of the signal measured by the optical detector at two distinct wavelengths. For instance, the property can be derived using a ratio of ratios (RoR) calculation according to the following equation:

$$\text{pulmonary oxygnation} \propto \frac{AC_1/DC_1}{AC_2/DC_2}$$

where $AC_1$ is the AC component of the signal measured by the optical detector at the first wavelength; $DC_1$ is the DC component of the signal measured by the optical detector at the first wavelength; $AC_2$ is the AC component of the signal measured by the optical detector at the second wavelength; and $DC_2$ is the DC component of the signal measured by the optical detector at the second wavelength.

Emitter/Detector Characteristics

In some embodiments, the one or more optical emitters can include solid state light sources such as GaAs, GaAlAs, GaAlAsP, GaAlP, GaAsP, GaP, GaN, InGaAlP, InGaN, ZnSe, or SiC light emitting diodes or laser diodes that excite the sensing one or more optical detectors at or near the wavelength of maximum absorption for a time sufficient to emit a return signal. However, it will be understood that in some embodiments the wavelength of maximum absorption/reflection varies as a function of the optical path from the one or more optical emitters to the one or more optical detectors.

In some embodiments, the one or more optical emitters can include other light emitting components including incandescent components. In some embodiments, the optical emitters can include a waveguide. The optical emitters can also include one or more filters such as bandpass filters, high pass filters, low pass filters, and/or other components such as antireflection elements, and/or focusing optics.

In some embodiments, the one or more optical emitters can include a plurality of LEDs with bandpass filters, with each of the LED-filter combinations emitting at a different center frequency. According to various embodiments, the LEDs can operate at different center-frequencies, sequentially turning on and off during a measurement. As multiple different center-frequency measurements are made sequentially, a single unfiltered optical detector can be used in some embodiments. However, in some embodiments, a polychromatic source can be used with multiple detectors that are each bandpass filtered to a particular center frequency.

The one or more optical detectors can be configured to receive light from the optical emitters. In an embodiment, the optical detectors can include a component to receive light. By way of example, in some embodiments, the optical detectors can include a charge-coupled device (CCD). In other embodiments, the optical detectors can include a photodiode, a junction field effect transistor (JFET) type optical sensor, or a complementary metal-oxide semiconductor (CMOS) type optical sensor. In some embodiments, the optical detectors can include an array of optical detecting components. In some embodiments, the optical detectors can include a waveguide. The one or more optical detectors can also include one or more bandpass filters and/or focusing optics. In some embodiments, the optical detectors can include one or more photodiode detectors, each with an optical bandpass filter tuned to a specific wavelength range.

Figure 26:
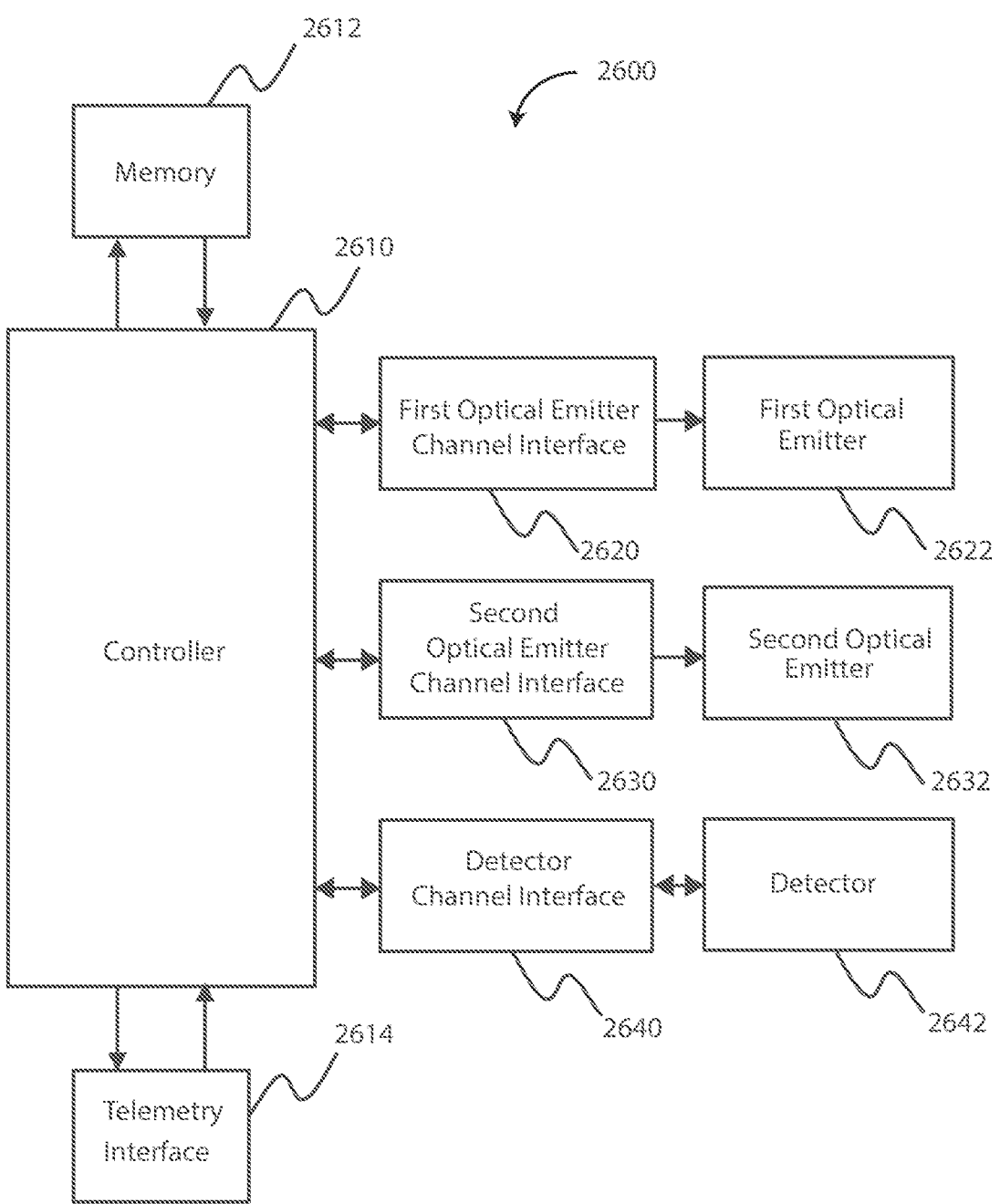
FIG. 26 is a schematic diagram of components of an oxygenation monitoring device in accordance with various embodiments herein.

Referring now to FIG. 26, a schematic block diagram of some components 2600 of an oxygenation monitoring device is shown in accordance with various embodiments herein. It will be appreciated that some embodiments can include additional elements beyond those shown in FIG. 26. In addition, some embodiments may lack some elements shown in FIG. 26. The implantable sensing devices herein can gather information through one or more detecting channels. A controller 2610 can communicate with a memory 2612 via a bidirectional data bus. It will be appreciated that controller 2610 can include one or more microprocessors. The memory 2612 can include read-only memory (ROM) or random-access memory (RAM) for program storage and RAM for data storage, or any combination thereof. The implantable medical device can include one or more optical emitters 2622, 2632, one or more detectors 2642, or one or more secondary sensors (not pictured). The one or more secondary sensors, but are not to be limited to, a pulse oximetry sensor, a chemical sensor, a posture sensor, or a heart rate sensor.

Each optical emitter 2622, 2632 is communicatively coupled to an optical emitter channel interface 2620, 2630. Each detector 2642 is communicatively coupled to a detector channel interface 2640. Each secondary sensor is communicatively coupled to a separate and secondary sensor channel interface (not pictured). Each of the optical emitter channel interfaces 2620, 2630, the detector channel interface 2640, and any of the other secondary sensor channel interfaces can communicate with controller 2610.

The first optical emitter channel interface 2620, the second optical emitter channel interface 2630, and the detector channel interface 2640 can each include various components such as analog-to-digital converters for digitizing signal inputs, sensing amplifiers, registers which can be written to by the control circuitry in order to adjust the gain and threshold values for the sensing amplifiers, source drivers, modulators, demodulators, multiplexers, and the like. A telemetry interface 2614 is also provided for communicating with external devices such as a programmer, a home-based unit, and/or a mobile unit (e.g., a cellular phone, portable computer, etc.), implanted devices such as a pacemaker, cardioverter-defibrillator, loop recorder, and the like.

Methods

Many different methods are contemplated herein, including, but not limited to, methods of making, methods of using, and the like. Aspects of system/device operation described elsewhere herein can be performed as operations of one or more methods in accordance with various embodiments herein.

Referring now to FIG. 27, a method 2700 for measuring an oxygenation status in a patient is shown in accordance with the embodiments herein. The method can include bringing an oxygenation monitoring device into contact with a tissue of the patient at 2702, where the oxygenation monitoring device can include a first optical emitter and a first optical detector. The method can include propagating an emitted light from the first optical emitter at a first wavelength from 100 nanometers (nm) to 2000 nm to a region of a lung tissue at 2704. The method can include detecting an incident light with the first optical detector at 2706. The method can include determining an oxygenation status of the lung tissue based on the detected incident light at 2708, where determining the oxygenation status comprises performing a ratiometric calculation using at least one of a measured light absorption, light scattering, or phase.

In an embodiment of the method, the optical sensor further comprises a second optical emitter configured to emit light at a second wavelength different than the first wavelength, where the ratiometric calculation is based on detecting incident light from the first optical emitter and second optical emitter.

In an embodiment, the method can further include implanting the oxygenation monitoring device subcutaneously at or near a site of a lung tissue so that the first optical emitter and the first optical detector are directed toward an interior of the patient toward a surface of the lung tissue.

In an embodiment of the method, the site is chosen based on whether the patient is likely to experience reduced ventilation or reduced perfusion.

In an embodiment, the site can include an upper portion of the lungs or a lower portion of the lungs.

In an embodiment of the method, the emitted light is propagated at a depth of from 1 cm to 5 cm into the lung tissue.

In an embodiment of the method, determining the oxygenation status of the lung tissue can include measuring at least one physical property of a lung tissue can include extravascular lung water, airway constriction, airway mucous, and airway inflammation.

In an embodiment, the method can further include monitoring a progression or regression of one or more conditions can include chronic obstructive pulmonary disease (COPD), pulmonary edema, asthma, pneumonia, airway obstruction, heart failure, acute respiratory distress syndrome (ARDS), septic shock, or pulmonary embolism.

In an embodiment, the method can further include measuring one or more of a heart rate, a respiratory rate, a tidal volume, circadian rhythm, posture, or an extravascular lung water concentration.

In an embodiment, the method can further include measuring one or more of a heart rate, a respiratory rate, a tidal volume, circadian rhythm, posture, or an extravascular lung water concentration to determine or interpret the oxygenation status.

In an embodiment, the method can further include measuring at least one of absorption, light scattering, or phase with the optical detector.

In an embodiment, the method can further include creating a composite score using at least two of the measured absorption, light scattering, or phase.

In an embodiment, the method can further include calculating an AC signal component and a DC signal component of the detected incident light to determine the oxygenation status of the lung tissue.

In an embodiment of the method, the AC signal component and the DC signal component are used for determining a ratio of ratios between the ratio of an AC signal component to a DC signal component at a first wavelength to the ratio of an AC signal component to a DC signal component at a second wavelength.

In an embodiment of the method, the AC signal component and the DC signal component are used for determining a ratio of ratios between the ratio of an AC signal component to a DC signal component at a first depth to the ratio of an AC signal component to a DC signal component at a second depth.

In an embodiment, the method can further include providing a therapy to the patient upon determining an oxygenation status of the lung tissue.

Systems

The devices herein can be used in various systems including multiple oxygenation monitoring devices and secondary sensors, including, but not limited to, methods of making, methods of using, and the like. Aspects of oxygenation monitoring devices described elsewhere herein can be included of one or more embodiments of a system in accordance with various embodiments herein.

In an embodiment, a sensor system is included for detecting an oxygenation status of a patient. The sensor system can include a first oxygenation monitoring device, the first oxygenation monitoring device including a first optical emitter, where the first optical emitter is configured to emit light at a first wavelength from 100 nm to 2000 nm. The system can further include a first optical detector, where the first optical detector is configured to detect incident light. The system can further include at least one secondary sensor comprising a pulse oximetry sensor, a chemical sensor, a posture sensor, or a heart rate sensor. In the systems described herein, the light from the first optical emitter can be configured to propagate through a lung tissue. In the systems described herein, the detected incident light and secondary sensor data can be used to determine an oxygenation status of the lung tissue.

In an embodiment of the system, determining the oxygenation status comprises performing a ratiometric calculation using at least one of a measured absorption, light scattering, or phase.

In an embodiment of the system, the system further includes a therapy interface configured to deliver a therapy to the patient after determining the oxygenation status of the lung tissue.

In an embodiment of the system, at least one of the oxygenation monitoring device or the secondary sensor is implantable.

In an embodiment of the system, the system further includes a second oxygenation monitoring device. The second oxygenation monitoring device can include a second optical emitter, where the second optical emitter can be configured to emit light at a second wavelength. The second oxygenation monitoring device can further include a second optical detector, where the second optical detector is configured to detect incident light.

It should be noted that, as used in this specification and the appended claims, the singular forms "a," "an," and "the"

include plural referents unless the content clearly dictates otherwise. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

As used herein, the recitation of numerical ranges by endpoints shall include all numbers subsumed within that range (e.g., 2 to 8 includes 2.1, 2.8, 5.3, 7, etc.).

The headings used herein are provided for consistency with suggestions under 37 CFR 1.77 or otherwise to provide organizational cues. These headings shall not be viewed to limit or characterize the invention(s) set out in any claims that may issue from this disclosure. As an example, although the headings refer to a "Field," such claims should not be limited by the language chosen under this heading to describe the so-called technical field. Further, a description of a technology in the "Background" is not an admission that technology is prior art to any invention(s) in this disclosure. Neither is the "Summary" to be considered as a characterization of the invention(s) set forth in issued claims.

The embodiments described herein are not intended to be exhaustive or to limit the invention to the precise forms disclosed in the following detailed description. Rather, the embodiments are chosen and described so that others skilled in the art can appreciate and understand the principles and practices. As such, aspects have been described with reference to various specific and preferred embodiments and techniques. However, it should be understood that many variations and modifications may be made while remaining within the spirit and scope herein.

The invention claimed is:

1. An oxygenation monitoring device comprising:
an implantable housing defining an interior volume, the implantable housing comprising:
control circuitry disposed within the interior volume;
a first optical emitter coupled to the implantable housing and in electrical communication with the control circuitry, wherein the first optical emitter is configured to emit light at a first wavelength from 100 nanometers (nm) to 2000 nm;
a second optical emitter coupled to the implantable housing and in electrical communication with the control circuitry, wherein the second optical emitter is configured to emit light at a second wavelength that is different from the first wavelength; and
a first optical detector coupled to the implantable housing and in electrical communication with the control circuitry, wherein the first optical detector is configured to detect incident light;
wherein the first optical emitter is spaced a first distance away from the first optical detector along a planar surface of the device;
wherein the second optical emitter is spaced a second distance away from the first optical detector along the planar surface of the device, wherein the first distance is greater than the second distance;
wherein the emitted light from the first optical emitter propagates through the lung tissue simultaneously with the emitted light from the second optical emitter;
wherein emitted light from the first optical emitter propagates through a lung tissue to a first depth; and
wherein emitted light from the second optical emitter propagates through the lung tissue to a second depth, wherein the first depth is greater than the second depth;
wherein the control circuitry determines an oxygenation status of the lung tissue using a ratio of a first molar extinction coefficient at the first wavelength to a second molar extinction coefficient at the second wavelength; and
wherein the device is implantable in a subcutaneous tissue of a patient.

2. The device of claim 1, wherein the device is configured so that emitted light from the first optical emitter propagates through tissue at a depth of at least 1 cm as measured from a surface of the device and back to the first optical detector.

3. The device of claim 1, wherein the first wavelength is from 550 nm to 1000 nm.

4. The device of claim 1, wherein the first optical emitter and the first optical detector are spaced along a length of the oxygenation monitoring device at from 1 cm to 10 cm apart.

5. The device of claim 1, wherein the first wavelength is from 600 nm to 800 nm.

6. The device of claim 1, wherein the second wavelength is from 800 nm to 2000 nm.

7. The device of claim 1, wherein emitted light from the first optical emitter is propagated to a different depth than emitted light from the second optical emitter.

8. The device of claim 1, wherein the device is further configured to determine one of a heart rate, a respiratory rate, a tidal volume, or an extravascular lung water concentration using a secondary sensor.

9. The device of claim 1, further comprising:
a flexible member, wherein the flexible member is connected to the housing and extends in a direction away from the implantable housing.

10. The device of claim 9, wherein at least one of the first optical emitter and the optical detector are disposed along a length of the flexible member.

11. The device of claim 1, wherein the first optical emitter and the optical detector are spaced along the planar surface of the device from 1 cm to 10 cm apart.

12. The device of claim 1, wherein propagation of the emitted light through a lung tissue comprises propagation of the emitted light from 1 cm to 5 cm in depth as measured from a surface of the oxygenation monitoring device.

13. The device of claim 1, wherein the first optical emitter is disposed at least 6 cm away from the first optical detector.

14. The device of claim 1, wherein the emitted light from the first optical emitter propagates through the lung tissue at a depth of at least 3 cm as measured from a surface of the device and back to the first optical detector.

15. A method for measuring an oxygenation status in a patient comprising:
bringing an oxygenation monitoring device into contact with a tissue of the patient, the oxygenation monitoring device comprising an optical sensor comprising:
an implantable housing defining an interior volume, the implantable housing comprising:
control circuitry disposed within the interior volume a first optical emitter coupled to the implantable housing and in electrical communication with the control circuitry, wherein the first optical emitter is configured to emit light at a first wavelength from 100 nanometers (nm) to 2000 nm;

a second optical emitter coupled to the implantable housing and in electrical communication with the control circuitry, wherein the second optical emitter is configured to emit light at a second wavelength that is different from the first wavelength; and a first optical detector coupled to the implantable housing and in electrical communication with the control circuitry, wherein the first optical detector is configured to detect incident light;

wherein the first optical emitter is spaced a first distance away from the first optical detector along a planar surface of the device;

wherein the second optical emitter is spaced a second distance away from the first optical detector along the planar surface of the device, wherein the first distance is greater than the second distance;

implanting the oxygenation monitoring device subcutaneously at or near a site of a lung tissue so that the first light emitter and the first light detector are directed toward an interior of the patient toward a surface of the lung tissue;

propagating a first emitted light from the first optical emitter at the first wavelength to a region of the lung tissue at a first depth;

propagating a second emitted light from the second optical emitter at the second wavelength to a second region of the lung tissue at a second depth, wherein the first depth is greater than the second depth;

wherein the emitted light from the first optical emitter propagates through the lung tissue simultaneously with the emitted light from the second optical emitter;

detecting an incident light with the optical detector;

determining an oxygenation status of the lung tissue based on the detected incident light;

wherein determining the oxygenation status comprises performing a ratiometric calculation using a ratio of a first molar extinction coefficient at the first wavelength to a second molar extinction coefficient at the second wavelength.

16. The method of claim 15, wherein the first emitted light is propagated at a depth of from 1 cm to 5 cm into the lung tissue.

17. The method of claim 15, further comprising monitoring a progression or regression of one or more conditions comprising chronic obstructive pulmonary disease (COPD), pulmonary edema, asthma, pneumonia, airway obstruction, heart failure, acute respiratory distress syndrome (ARDS), septic shock, or pulmonary embolism.

* * * * *